(12) United States Patent
Wanasek

(10) Patent No.: US 8,504,154 B2
(45) Date of Patent: Aug. 6, 2013

(54) PHYSIOLOGICAL SIGNAL AMPLIFIER WITH VOLTAGE PROTECTION AND FAST SIGNAL RECOVERY

(75) Inventor: Kevin A. Wanasek, Princeton, MN (US)

(73) Assignee: Medtronic, Inc., Minneapolis, MN (US)

( * ) Notice: Subject to any disclaimer, the term of this patent is extended or adjusted under 35 U.S.C. 154(b) by 1031 days.

(21) Appl. No.: 12/414,216

(22) Filed: Mar. 30, 2009

(65) Prior Publication Data
US 2010/0249867 A1 Sep. 30, 2010

(51) Int. Cl.
*A61N 1/08* (2006.01)
(52) U.S. Cl.
USPC .................................. 607/28; 607/36; 607/37
(58) Field of Classification Search
USPC .............................................. 607/28, 36, 37
See application file for complete search history.

(56) References Cited

U.S. PATENT DOCUMENTS

| 3,569,852 | A | | 3/1971 | Berkovits |
| 4,216,780 | A | | 8/1980 | Rubel et al. |
| 4,304,238 | A | * | 12/1981 | Fischer ........................... 607/31 |
| 4,914,400 | A | | 4/1990 | Kobayashi et al. |
| 5,333,617 | A | | 8/1994 | Hafner |
| 5,591,218 | A | * | 1/1997 | Jacobson ........................ 607/63 |
| 6,411,844 | B1 | | 6/2002 | Kroll et al. |
| 6,647,289 | B2 | * | 11/2003 | Prutchi ........................ 600/547 |
| 6,897,731 | B2 | | 5/2005 | Zhang et al. |

FOREIGN PATENT DOCUMENTS

WO 2005/115538 A1 12/2005

OTHER PUBLICATIONS (PCT/US2010/025569) PCT Notification of Transmittal of the International Search Report and the Written Opinion of the International Searching Authority, Jun. 10, 2005.

* cited by examiner

*Primary Examiner* — Joseph Dietrich
(74) *Attorney, Agent, or Firm* — Evans M. Mburu; Stephen W. Bauer

(57) ABSTRACT

A physiological sense amplifier achieves fast recovery times following receipt of a large voltage, such as when a defibrillation pulse is delivered, without blanking. The recovery time may be less than one millisecond when polarization of surrounding tissue or the housing of the device is not present. The sense amplifier uses a feedback network to clamp the input voltage to a gain amplifier at a predetermined value when a predetermined threshold value is exceeded.

27 Claims, 12 Drawing Sheets

PHYSIOLOGICAL SIGNAL AMPLIFIER WITH VOLTAGE PROTECTION AND FAST SIGNAL RECOVERY

TECHNICAL FIELD

The invention relates to medical devices and, more particularly, medical devices that sense physiological signals.

BACKGROUND

A variety of medical devices have been used or proposed for use for delivering a therapy to and/or monitoring a physiological condition of patients. Some medical devices are entirely or primarily located external to the body of the patient, which others are implantable within the patient. Some medical devices employ stimulation electrodes, sense electrodes, and/or other sensors. Medical devices deliver electrical stimulation to, and/or monitor conditions associated with, the heart, muscle, nerve, brain, stomach, or other organs or tissue. In some examples, electrodes or sensors detect the presence or concentration of proteins or chemicals within the blood or other bodily fluids.

Medical leads are configured to allow electrodes or sensors to be positioned at desired locations for delivery of stimulation or sensing. For example, with a proximal portion of the lead coupled to a medical device housing, electrodes or sensors may be located on a distal portion of a lead. Other medical devices include electrodes or sensors on or within the device, or are coupled to sensors wirelessly, and therefore need be coupled to medical leads.

Cardiac pacemakers or cardioverter-defibrillators, for example, provide therapeutic electrical stimulation to the heart via electrodes carried by one or more leads. The electrical stimulation may include signals such as pulses or shocks for pacing, cardioversion or defibrillation. In some cases, a medical device senses intrinsic depolarizations of the heart, and controls delivery of stimulation signals to the heart based on the sensed depolarizations. Upon detection of an abnormal rhythm, such as bradycardia, an appropriate electrical pacing stimulation signal or signals are delivered to maintain or restore a normal rhythm. In some cases, a medical device delivers rapid pacing pulses to the heart of the patient upon detecting tachycardia. High voltage shocks can be delivered for the purpose of cardioversion of a tachycardia, or for defibrillation of the heart upon detecting fibrillation.

In general, cardiac pacemakers, cardioverters, and/or defibrillators include physiological sense amplifiers coupled to electrodes to detect cardiac electrical signals associated with the depolarization and repolarization the heart, which may be used for a variety of purposes in addition to determining heart rate. For example, cardiac electrical signals may be used for rhythm classification, which may include morphological or other analysis of the signal. As another example, cardiac electrical signals may also be stored for later review by a clinician, e.g., for evaluation or diagnosis. Other implantable or external devices also include physiological sense amplifiers for sensing other physiological signals, such as neurological signals.

The physiological sense amplifiers amplify physiological signals whose amplitudes are typically 20 mV or less, and, in some cases, also filter the sensed physiological signals to increase the signal-to-noise ratio (SNR) prior to processing the signal. However, large voltage signals, such as pacing pulses or shocks for cardioversion or defibrillation, saturate the sense amplifier. Saturation of the amplifier may render the output of the amplifier unusable. For example, when the amplifier is saturated, the information from the sensed signal may not be present in the output of the amplifier. Polarization of the myocardial tissue proximate to electrodes or of the device housing, which can itself act as a stimulation and/or sensing electrode, may also lead to saturation of the sense amplifier.

The time in which it takes the sense amplifier to return from saturation to a normal sensing state may be referred to as the recovery time. The recovery time may last for several seconds. For this reason, the sense amplifier is often blanked during delivery of a pulse or shock to avoid saturation of the sense amplifier. Blanking decouples the sense amplifier inputs from electrodes. Blanking typically extends beyond the duration of the electrical stimulus for a period of time, referred to as a blanking period.

SUMMARY

This disclosure describes a signal conditioning physiological sense amplifier for use in a medical device. The sense amplifier may be used independently, or as part of a more complex sense amplifier in the medical device. The sense amplifier may be used in an implantable medical device (IMD), such as an implantable pacemaker, cardioverter, and/or defibrillator, or an implantable neurostimulator (INS), or any other implantable device. In other examples, the sense amplifier is used in an external device, such as an external pacemaker, external defibrillator, external neurostimulator, external pulse generator, or external monitor.

The sense amplifier is configured to achieve fast recovery times following receipt of a large voltage, e.g., following delivery of cardioversion or defibrillation pulses to the heart, without blanking. The ability to quickly recover from a large voltage may be particularly advantageous in situations in which the sense amplifier could not be blanked because the applied voltage could not be anticipated, such as when the sense amplifier is located in a first device and a second device delivers a cardioversion or defibrillation pulse. The recovery time of this sense amplifier may be less than approximately one millisecond when polarization of surrounding tissue or the housing of the device is not present.

The sense amplifier uses a feedback network to clamp the input voltage to a gain amplifier at a predetermined value to achieve the fast recovery time without decoupling the sense amplifier. In operation, and more particularly when a small amplitude signal such as an electrical cardiac signal is present at the input, the feedback network does not provide clamping and allows the small amplitude signal to be amplified by the gain amplifier. However, when presented a larger voltage, the clamping feature of the feedback network is activated and clamps the input voltage to the gain amplifier at the predetermined value.

The sense amplifier includes a high pass filter that includes a capacitor which would store a large direct current (DC) voltage if the input voltage to the gain stage was not clamped for the duration of the therapy pulse. The feedback network, when activated by a large amplitude signal at the input to the gain stage, connects the high pass filter capacitor to a lower resistance current path that allows the high pass filter capacitor to discharge, or charge depending on the polarity of the voltage, more quickly than would otherwise be possible. The lower resistance current path clamps the input voltage to the gain stage at the predetermined value and also shifts the pole of the high pass filter. Thus, the sense amplifier may also be described as using a pole shifting technique to achieve fast recovery times without blanking.

In some examples, the sense amplifier also includes a time delay for preventing the output of the sense amplifier from false level sensing. After the therapy pulse or other large voltage has ended, tissue surrounding the electrodes and/or the housing of the IMD may be polarized with a decaying DC voltage. Without a time delay, the electrical cardiac signals ride on the DC signal and may be falsely detected as multiple cardiac events by subsequent processing circuitry. The time delay keeps the clamping feature of the feedback network activated for a period of time after the therapy pulse has ended, thereby allowing the DC polarization to dissipate. After the time delay is over, the clamping feature of the feedback network is deactivated, and the sense amplifier returns to normal operation, i.e., amplifying small amplitude signals.

Additionally, the sense amplifier may include circuitry for blocking potentially harmful voltage levels from damaging the sense amplifier. This voltage blocking circuitry may include a pair of high voltage transistors coupled to the inputs of an instrumentation amplifier. The high voltage transistors may be biased so that they operate in an analog mode that clamps the voltage at the source when the gate-to-source on threshold voltage is no longer exceeded. In one example, the transistors clamp the voltage at approximately 2.5 V.

In one example, a physiological sense amplifier configured for use in a medical device to sense a physiological electrical signal of a patient comprises a high pass filter comprising a capacitor and a resistor coupled in series, wherein a voltage applied across the resistor is proportional to the physiological electrical signal, an amplifier that amplifies an input voltage to generate an output voltage, wherein the input voltage is a function of the voltage applied to the resistor when the input voltage is less than a predetermined threshold value, and a feedback network comprising a transistor coupled in parallel with the resistor. The output voltage of the amplifier is coupled to a control terminal of the transistor to activate the transistor when the input voltage exceeds the predetermined threshold value, and the transistor clamps the input voltage of the amplifier to a substantially constant value when the transistor is activated.

In another example, a medical device comprises a sense amplifier that receives a differential voltage from first and second electrodes, outputs a voltage proportional to the differential voltage when the differential voltage is less than a predetermined threshold value, and outputs a substantially constant voltage when the differential voltage exceeds the predetermined threshold value. The medical device further comprises a processor to process the output of the sense amplifier to sense a physiological signal of a patient. The sense amplifier comprises a high pass filter comprising a capacitor and a resistor coupled in series, wherein a voltage applied across the resistor is proportional to the physiological electrical signal, an amplifier that amplifies an input voltage to generate an output voltage, wherein the input voltage is a function of the voltage applied to the resistor when the input voltage is less than a predetermined threshold value, and a feedback network comprising a transistor coupled in parallel with the resistor. The output voltage of the amplifier is coupled to a control terminal the transistor to activate the transistor when the input voltage exceeds the predetermined threshold value, and the transistor clamps the input voltage of the amplifier to a substantially constant value when the transistor is activated.

In another example, a medical system comprises a first medical device configured to deliver an electrical stimulation signal to a patient, and a second medical device configured to sense a physiological electrical signal of the patient. The second medical device comprises a sense amplifier that receives a differential voltage from first and second electrodes, outputs a voltage proportional to the differential voltage when the differential voltage is less than a predetermined threshold value, and outputs a substantially constant voltage when the differential voltage exceeds the predetermined threshold value, wherein the electrical stimulation signal delivered by the first medical device causes the differential voltage to exceed the predetermined threshold value. The second medical device further comprises a processor to process the output of the sense amplifier to sense a physiological signal of a patient. The sense amplifier comprises a high pass filter comprising a capacitor and a resistor coupled in series, wherein a voltage applied across the resistor is proportional to the physiological electrical signal, an amplifier that amplifies an input voltage to generate an output voltage, wherein the input voltage is a function of the voltage applied to the resistor when the input voltage is less than a predetermined threshold value, and a feedback network comprising a transistor coupled in parallel with the resistor. The output voltage of the amplifier is coupled to a control terminal of the transistor to activate the transistor when the input voltage exceeds the predetermined threshold value, and the transistor clamps the input voltage of the amplifier to a substantially constant value when the transistor is activated.

DETAILED DESCRIPTION

Figure 1:
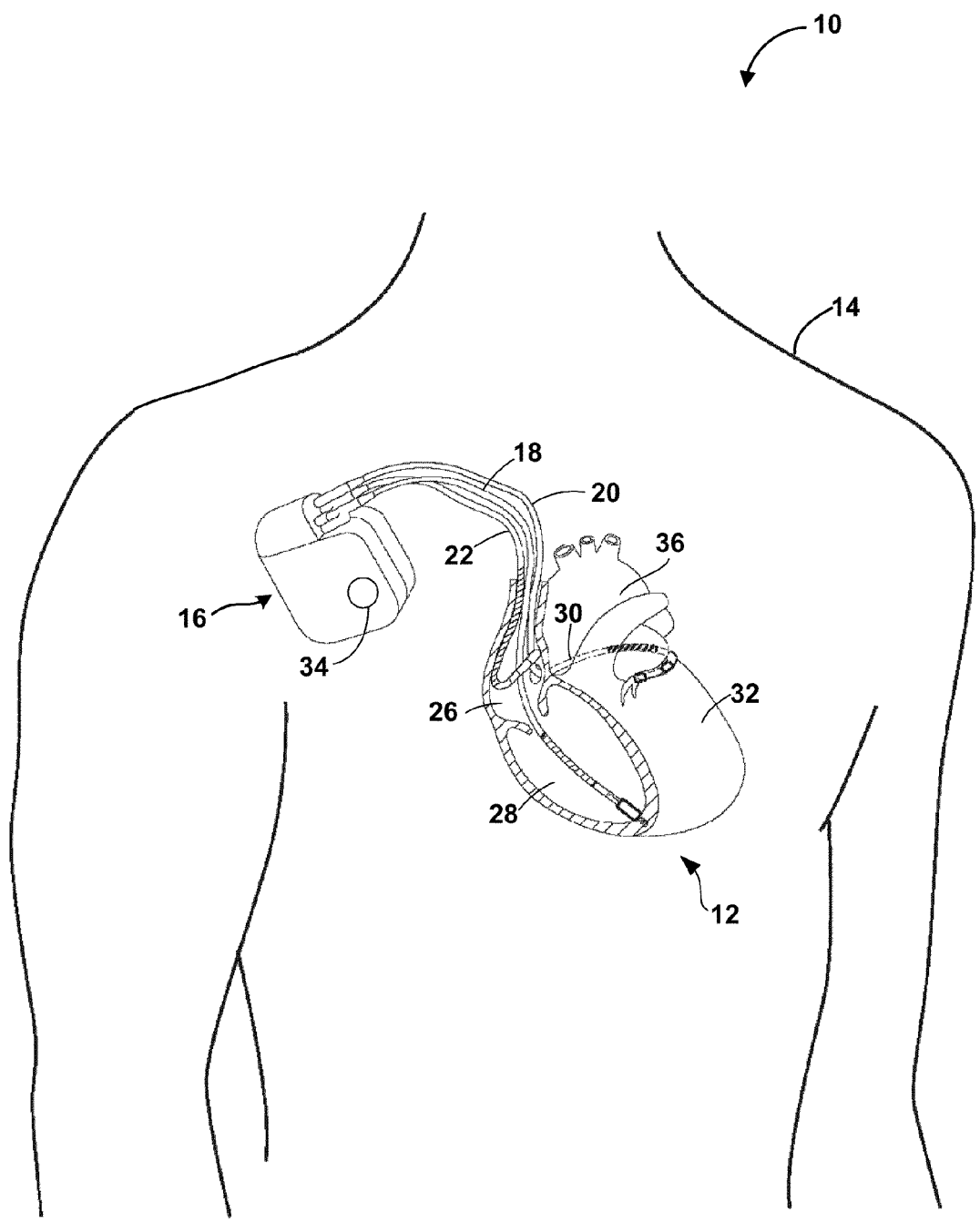
FIG. 1 is a conceptual diagram illustrating an example system that includes an implantable cardiac device (ICD) with a fast recovery signal conditioning physiological amplifier for monitoring a heart of a patient.

FIG. 1 is a conceptual diagram illustrating an example system 10 including an implantable cardiac device (ICD) 16 that monitors and delivers therapy to heart 12 of patient 14. ICD 16 includes a signal conditioning physiological sense amplifier, described in greater detail below, that achieves fast recovery times following delivery of therapy to heart 12 without blanking. The recovery time may be less than approximately one millisecond (ms) when polarization of surrounding tissue or the housing of ICD 16 is not present.

In the illustrated example, ICD 16 is coupled to leads 18, 20, and 22. ICD 16 delivers electrical signals to heart 12 and senses electrical signals attendant to the depolarization and repolarization of heart 12 via electrodes (not shown) coupled to one or more of leads 18, 20, and 22 and, in some cases, a housing electrode (not shown) of ICD 16. ICD 16 may operate as an implantable pacemaker, a cardioverter, and/or defibrillator.

Right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12. Other configurations, i.e., number and position of leads, are possible.

After an electrical pulse is delivered to the heart, it may be important to monitor the heart in order to determine the condition of the patient. In particular, it is important to determine if the therapy was effective and, if not, to deliver additional appropriate therapy. The fast recovery signal conditioning physiological sense amplifier of ICD 16 allows ICD 16 to, without blanking, sense electrical cardiac signals of heart 12 substantially immediately after an electrical pulse is delivered to the heart. Throughout this disclosure substantially immediately is used with reference to the recovery period of the signal conditioning physiological sense amplifier, which may be less than one millisecond (ms) when polarization of tissue surrounding ICD 16 or of the housing of ICD 16 is not present.

The sense amplifier of ICD 16 uses a feedback network to clamp the input voltage to the gain amplifier at a predetermined value to achieve the fast recovery time without blanking. Generally, the sense amplifier includes a high pass filter for removing or suppressing direct current (DC) signals and a gain amplifier for increasing the signal-to-noise ratio (SNR) of the sensed signal. The high pass filter may be a resistor-capacitor (RC) high pass filter with a relatively low cutoff frequency for filtering DC signals but passing electrical cardiac signals. Example circuit diagrams for the sense amplifier are provided in FIGS. 6-10.

Generally, the sense amplifier operates in two different modes. In a first mode, the sense amplifier operates normally, i.e., as an amplifier that amplifies electrical cardiac signals sensed via electrodes carried on one or more of leads 18, 20, 22, and, in some cases, a housing electrode of ICD 16. The feedback network is not activated when the sense amplifier operates in the first mode, i.e., does not provide clamping feedback. The sense amplifier operates in this first mode when the input voltage at the gain amplifier is less than a predetermined threshold voltage. The value of the threshold voltage is selected to be greater than the value of a typical electrical cardiac signal or other physiological signal, and less than the value of a pacing or cardioversion/defibrillation pulse. For example, the value may be selected within a range of approximately 30 millivolts (mV) to approximately 1 Volt (V), since an electrical cardiac signal is typically less than 20 mV and a typical pacing pulse is greater than 1 V. Throughout this disclosure, an example threshold value of 420 mV is used. The predetermined threshold value may be configurable by selection of circuit components and values, such as resistance or voltage, in a sense amplifier circuit, such as those illustrated in FIGS. 6-10.

The sense amplifier operates in a second mode when the voltage at an input to the gain amplifier is greater than the predetermined threshold value. When operating in the second mode, the sense amplifier activates the feedback network to clamp the input voltage to the gain amplifier at the predetermined threshold value. In particular, when activated, the feedback network connects the high pass filter capacitor to a lower resistance current path that allows the high pass filter capacitor to discharge, or charge depending on the polarity of the therapy pulse, more quickly than would otherwise be possible. This clamps the input voltage to the input of the gain amplifier and results in a fast recovery time for the amplifier post therapy.

The lower resistance current path shifts the pole of the high pass filter so that the cutoff frequency of the high pass filter increases. For example, the cutoff frequency of the high pass filter when the sense amplifier operates in the first mode may be a relatively low frequency, e.g., less than one Hertz (Hz), for blocking direct current. The cutoff frequency shifts to a higher value when the sense amplifier operates in the second mode. In particular, the cutoff frequency may shift such that it is higher than the frequency of the pacing or cardioversion/defibrillation pulse. As an example, the cutoff frequency of the high pass filter may be approximately 0.15 Hz when operating in the first mode and shift to approximately 1 MHz or higher when operating in the second mode. For this reason, the sense amplifier may also be described as using a pole shifting technique to achieve fast recovery times without blanking.

The sense amplifier may also implement a time delay that prevents false level sensing. After the therapy pulse has ended, tissue surrounding the electrodes and/or the housing of ICD 16 itself may be polarized and the electrical cardiac signal may ride on the DC polarization signal. Without the time delay, the sense amplifier may return to operating in the first mode, which may result in ICD 16 falsely detecting multiple cardiac events based on the DC-shifted signal. The time delay, however, delays ICD 16 from returning to operating in the first mode when the therapy pulse ends. This allows the DC polarization to dissipate before ICD 16 returns to operating in the first mode.

Because the circuit elements for the sense amplifier may be low voltage components, and the therapy pulses (pacing, cardioversion, or defibrillation pulses) may have relatively high voltages, the sense amplifier may include a voltage blocking circuitry at the front end. As examples, the circuit elements for the sense amplifier may have a voltage rating less than or equal to approximately 6 V, or less than or equal to approximately 3.3 V. As examples, therapy pulse voltages may be approximately 1 V or more for a pacing pulse delivered by implanted medical leads up to approximately 800 V for implanted cardioversion and defibrillation pulses, and may be significantly higher for a defibrillation pulse delivered via external electrodes placed on the body of the patient. In this disclosure, the front end of the sense amplifier is used to refer to the voltage blocking components of the circuit and the back end of the circuit is used to refer to the actual sensing amplifier that uses a feedback network to provide fast recovering times post "therapy" without blanking.

In one example, the front end of the sense amplifier uses a pair of transistors coupled to the inputs. For example, one transistor may be coupled to one sense electrode and the other transistor may be coupled to the other sense electrode. The transistors are used to sense the differential voltage across the electrodes and are coupled to the inputs of the back end of the signal conditioning physiological sense amplifier. As described in greater detail with respect to the circuit diagrams of FIGS. 6-10, the inputs to the back end of the sense amplifier may be the inputs of an instrumentation amplifier used to convert the differential voltage signal to a single-ended signal. The transistors may also be coupled to each other through a reference potential, i.e., a reference ground for the sense amplifier. The gate voltage for each of the transistors is controlled so that when the gate-to-source on threshold voltage of the transistor no longer exceeds a predetermined value, the transistors operate in an analog mode. In an analog mode, the transistor clamps the voltage at the source at a substantially constant value, thereby blocking the back end of the sense amplifier from potentially harmful voltage levels. For example, the transistors may be configured to clamp the voltage at approximately 2.5 V. Accordingly, this front end may shunt relatively little energy away from the heart. Additionally, because the transistors may be implemented as high voltage parts, e.g., transistors with a voltage rating of 1200 V, the front end may provide increased reliability over other clamping devices, such as transient voltage suppressors or diodes that shunt energy away from the heart.

The fast recovery signal conditioning physiological sense amplifier may provide certain advantages over typical physiological sense amplifiers. Typical physiological sense amplifiers rely on blanking to avoid long saturation periods. The described signal conditioning physiological sense amplifier, however, does not require blanking and may achieve a recovery time of less than approximately one millisecond when polarization is not present. Furthermore, the described sense amplifier may provide advantages for automatically setting pacing amplitude. In particular, the described sense amplifier may be able to recover quickly enough after a pacing pulse to detect an evoked response by the heart from the pacing pulse that may be used to determine the pacing capture threshold. The fast recovery time of described sense amplifier may also provide advantages for other signal analyses.

A signal conditioning physiological sense amplifier according to the disclosure may be particularly advantageous in situations in which blanking is not possible. Some example systems in which blanking is not possible include systems having two or more medical devices that do not communicate to coordinate blanking. In such systems, when one medical device delivers a stimulation pulse, a signal conditioning physiological sense amplifier according to this disclosure in another medical device may be protected from and recover relatively quickly from the unanticipated voltage. Example systems with multiple medical devices are shown in FIGS. 2 and 3.

Figure 2:
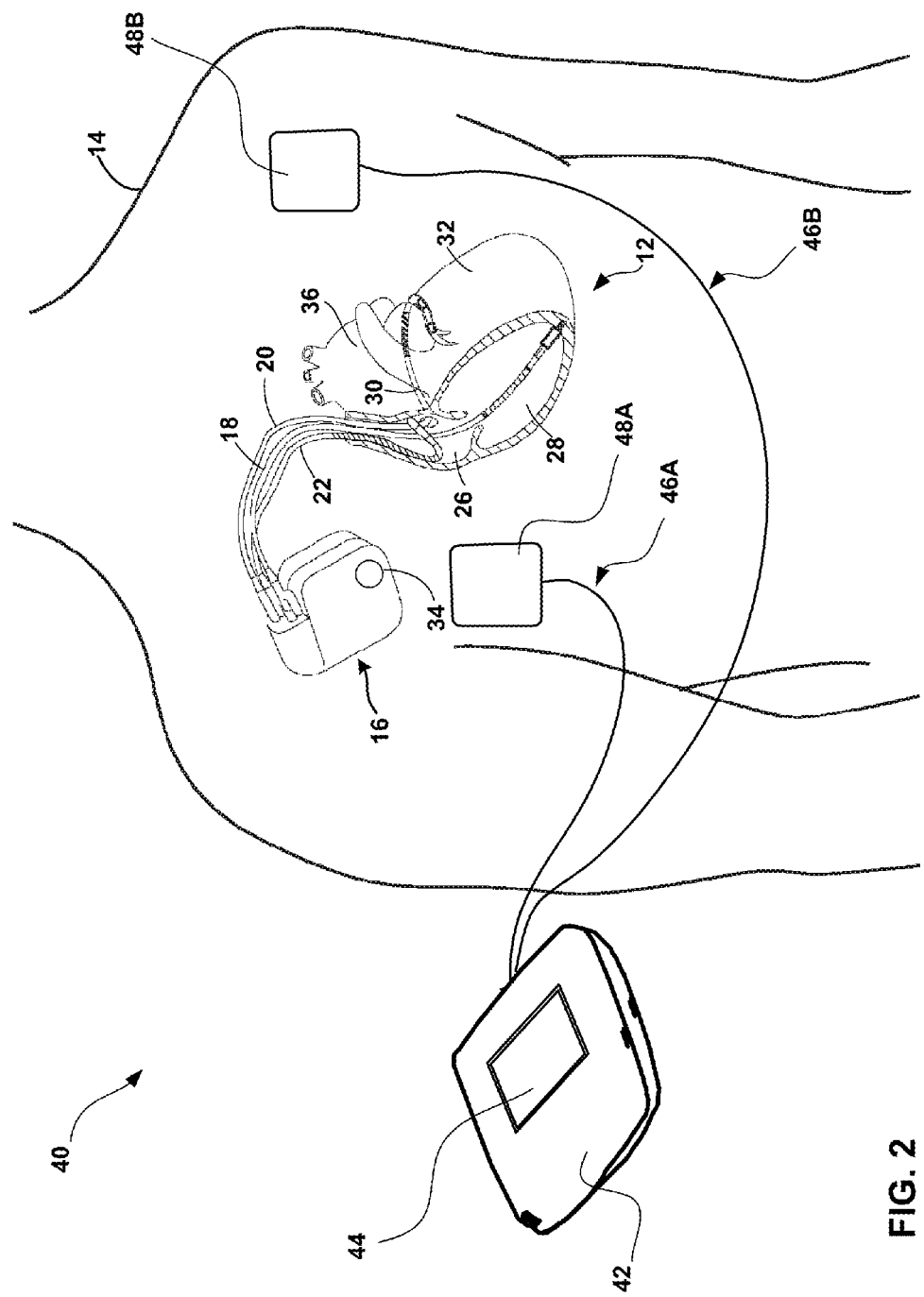
FIG. 2 is a conceptual diagram illustrating another example system that includes an automated external defibrillator (AED) and ICD configured with a fast recovery signal conditioning physiological amplifier.
Figure 3:
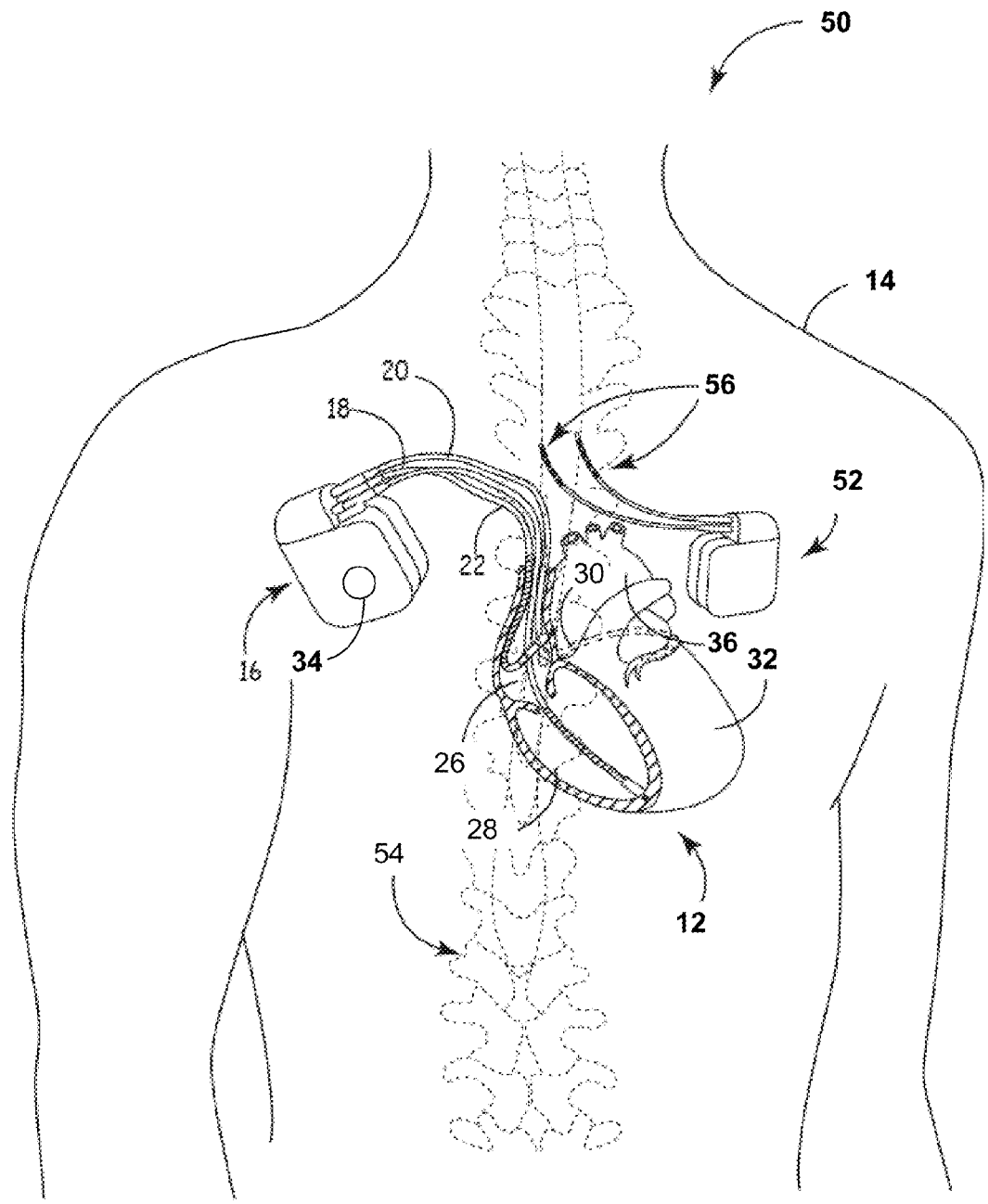
FIG. 3 is a conceptual diagram illustrating another example system that includes an ICD that provides therapy to the heart of a patient and an implantable neurostimulator that is configured with a fast recovery signal conditioning physiological amplifier for monitoring neurological signals of a patient.

FIG. 2 is a conceptual diagram illustrating another example system 40 that includes an external defibrillator 42 and ICD 16. External defibrillator 42 may be, for example, an automated external defibrillator (AED), or a more fully featured external defibrillator. ICD 16, external defibrillator 42, or both ICD 16 and external defibrillator 42, may be configured with a fast recovery signal conditioning physiological sense amplifier.

In the illustrated example, external defibrillator 42 is coupled to two electrodes 48A and 48B (collectively "electrodes 48") that are applied to the surface, e.g., skin, of patient 14. Electrodes 48 are coupled to defibrillator 42 by respective leads or cables 46A and 46B (collectively "cables 46"). External defibrillator 42 detects electrical activity of the heart 12 of patient 14 via electrodes 48, and delivers electrical stimulation to heart 12 via electrodes 48. For example, defibrillator 42 may detect tachyarrhythmia and deliver one or more responsive defibrillation pulses to patient 14 via electrodes 48. As shown in FIG. 2, defibrillator 42 includes a display 44, which may display an electrocardiogram generated based on the electrical activity detected by electrodes 48 via display 44.

In some examples, ICD 16 and external defibrillator 42 are not configured to communicate with each other. Accordingly, ICD 16 and external defibrillator 42 may not operate in a coordinated fashion and, thus, ICD 16 and defibrillator 42 may be unaware of when the other of the ICD and defibrillator delivers therapy to heart 12. However, in examples in which ICD 16 is configured with a fast recovery signal conditioning physiological sense amplifier according to the disclosure, ICD 16 may be able to more effectively and quickly monitor cardiac electrical signals after external defibrillator 42 delivers a therapeutic pulse, e.g., a defibrillation shock, to patient 14. ICD 16 may additionally be configured to withhold therapy based on the detection of external shocks from defibrillator 42, or go into a diagnostic mode to record events, or deliver additional therapy to complement therapy delivered by defibrillator 42. Furthermore, in examples in which external defibrillator 42 is configured with the fast recovery physiological sense amplifier described in this disclosure, external defibrillator 42 may be able to more effectively and quickly monitor cardiac electrical signals, or display a useful electrocardiogram signal on display 44, after ICD 16 delivers a therapeutic pulse. Additionally, both ICD 16 and defibrillator 42 may be protected from being damaged by therapy delivered by the other device.

FIG. 3 is a conceptual diagram illustrating another example system 50 that includes ICD 16 and an implantable neurostimulator (INS) 52. In some cases, ICD 16 and INS 52 are not configured to communicate with each other. Additionally, therapy pulses delivered by ICD 16 to heart 12 may be sensed by INS 52 and, similarly, stimulation pulses delivered by INS 52 may be sensed by ICD 16. In the illustrated example, one or both of INS 52 and ICD 16 may be configured with a fast recovery signal conditioning physiological sense amplifier as described in this disclosure to facilitate sensing recovery after delivery of a stimulation pulse by the other device and provide protection from the unanticipated stimulation pulse.

INS 52 may be any suitable implantable medical device that includes a signal generator for generating electrical stimulation signals that may be delivered to tissue of patient 12, e.g., neural tissue. Example target stimulation sites include the tissue proximate the spinal cord 54, brain, vagus nerve, or peripheral nerves. INS 52 delivers the stimulation via one or more leads 56. INS 52 may be subcutaneously or submuscularly implanted in the body of a patient 14, e.g., in a chest cavity, lower back, lower abdomen, or buttocks of patient 14.

In some examples, INS 52 delivers electrical stimulation to an autonomic nerve, i.e., sympathetic and/or parasympathetic nerve, such as the vagus nerve, of patient 12. Stimulation of a parasympathetic nerve, for example, may help slow intrinsic rhythms of heart 12 or decrease irritability of heart 12, which may compliment antitachyarrhythmia therapy (e.g., antitachycardia pacing, cardioversion or defibrillation) delivered by ICD 16, or more generally control a heart rate of patient 12.

INS 52 may sense electrical signals, e.g., neurological or cardiac signals, via electrodes located on leads 56 or a housing of the INS. In some examples, INS 52 controls delivery of neurostimulation as a function of the sensed signals. A fast recovery signal conditioning physiological sense amplifier according to this disclosure may allow sensing by enabling INS 52 to recover from delivery of stimulation by ICD 16 without blanking. Similarly, a fast recovery signal conditioning physiological sense amplifier according to this disclosure may allow sensing by enabling ICD 16 to recover from delivery of stimulation by INS 52 without blanking. Additionally, the voltage blocking front end of the sense amplifier of this disclosure may protect both INS 52 and ICD 16 from the unanticipated high voltage therapies delivered by the other device.

It should be understood that the systems shown in FIGS. 1-3 represent only some of the possible systems in which a fast recovery signal conditioning physiological sense amplifier may be used. As another example, a system may comprise a pacemaker implanted in a patient and a subcutaneous cardioverter/defibrillator subsequently implanted in the patient to provide cardioversion and/or defibrillation therapy not provided by the pacemaker. One or both of the pacemaker or subcutaneous cardioverter/defibrillator may include a fast recovery signal conditioning physiological sense amplifier as described herein, which may facilitate monitoring cardiac electrical signals after the other device delivers a therapeutic pulse, or coordination of therapy or delivery of complimentary therapies by the devices. Other systems may include an external temporary pacemaker or other device comprising an external pulse generator configured with the described sense amplifier. Generally, the described sense amplifier may be used in any system that includes a medical device for monitoring physiological signals a patient.

Figure 4:
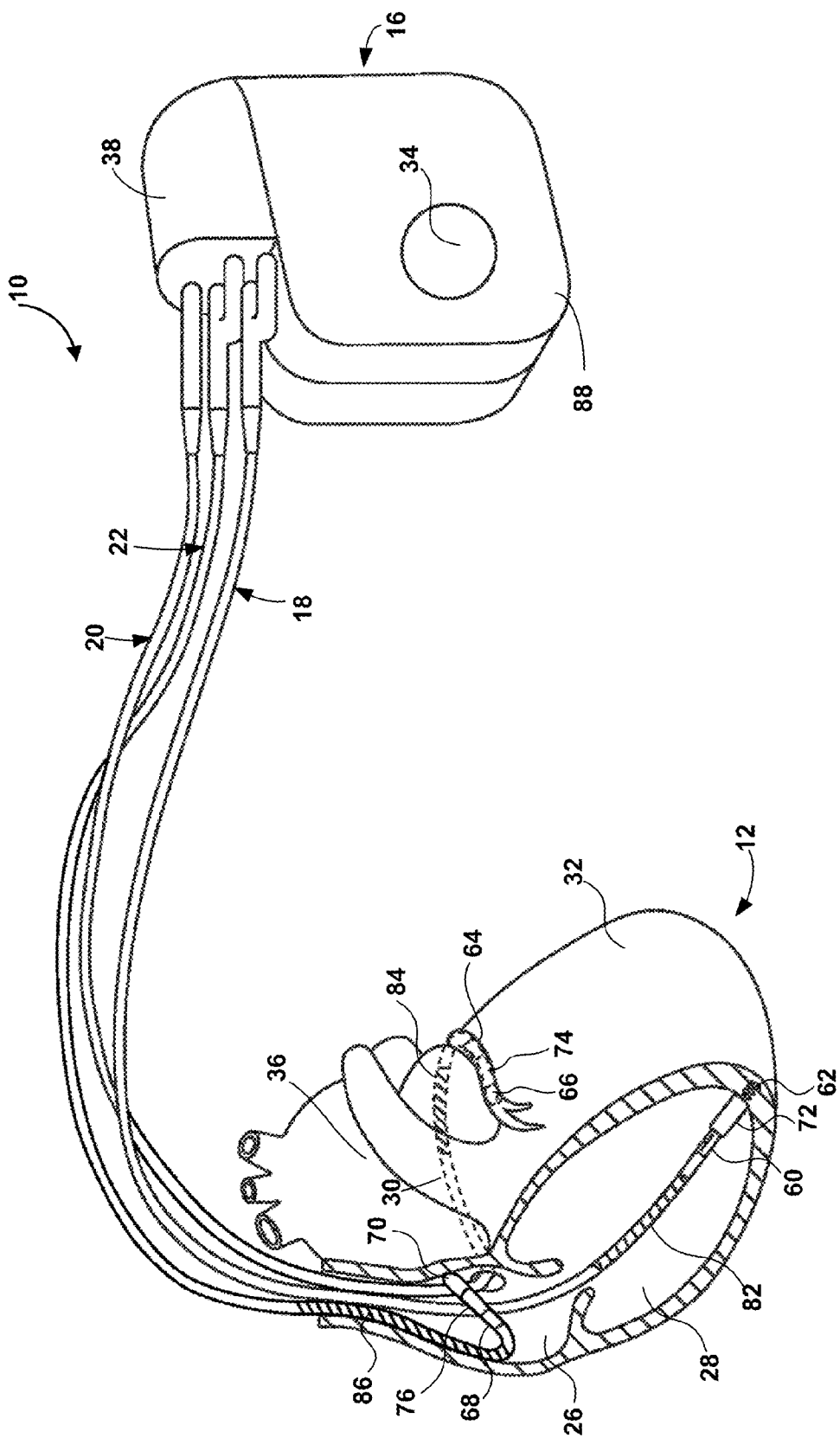
FIG. 4 is a conceptual diagram illustrating the ICD and leads of the system shown in FIG. 1 in greater detail.

FIG. 4 is a conceptual diagram illustrating ICD 16 and leads 18, 20, and 22 in greater detail. Each of the leads 18, 20, 22 includes an elongated insulative lead body, which may carry a number of conductors. Bipolar electrodes 60 and 62 are located adjacent to a distal end of lead 18. In addition, bipolar electrodes 64 and 66 are located adjacent to a distal end of lead 20, and bipolar electrodes 68 and 70 are located adjacent to a distal end of lead 22. Furthermore, each of leads 18, 20, 22 includes a respective one of elongated electrodes 82, 84, 86. Each of the electrodes 60, 62, 64, 66, 68, 70, 82, 84 and 86 is electrically coupled to a respective one of the conductors within the lead body of its associated lead 18, 20, 22, and thereby coupled to signal generation and sensing circuitry within ICD 16.

ICD 16 includes one or more housing electrodes, such as housing electrode 34, which may be formed integrally with an outer surface of hermetically-sealed housing 88 of ICD 16 or otherwise coupled to housing 88. In some examples, housing electrode 34 is defined by an uninsulated portion of an outward facing portion of housing 88 of ICD 16. Other division between insulated and uninsulated portions of housing 88 may be employed to define two or more housing electrodes. In some examples, housing electrode 34 comprises substantially all of housing 88. As described in further detail with reference to FIG. 5, housing 88 may enclose a signal generator that generates therapeutic stimulation, such as cardiac pacing pulses and defibrillation shocks, as well as a sensing module for monitoring the rhythm of heart 12 in the body of patient 14. The sensing module may include one or more fast recovery physiological sense amplifiers as described in this disclosure.

ICD 16 senses electrical signals attendant to the depolarization and repolarization of heart 12 via selected combinations of electrodes 34, 60, 62, 64, 66, 68, 70, 82, 84 and 86. In some examples, ICD 16 delivers pacing pulses via bipolar combinations of electrodes 60, 62, 64, 66, 68 and 70 to produce depolarization of cardiac tissue of heart 12. In some examples, ICD 16 delivers pacing pulses via any of electrodes 60, 62, 64, 66, 68 and 70 in combination with housing electrode 34 in a unipolar configuration. Furthermore, ICD 16 may deliver cardioversion or defibrillation pulses to heart 12 via any combination of elongated electrodes 82, 84, 86, and housing electrode 34.

Figure 5:
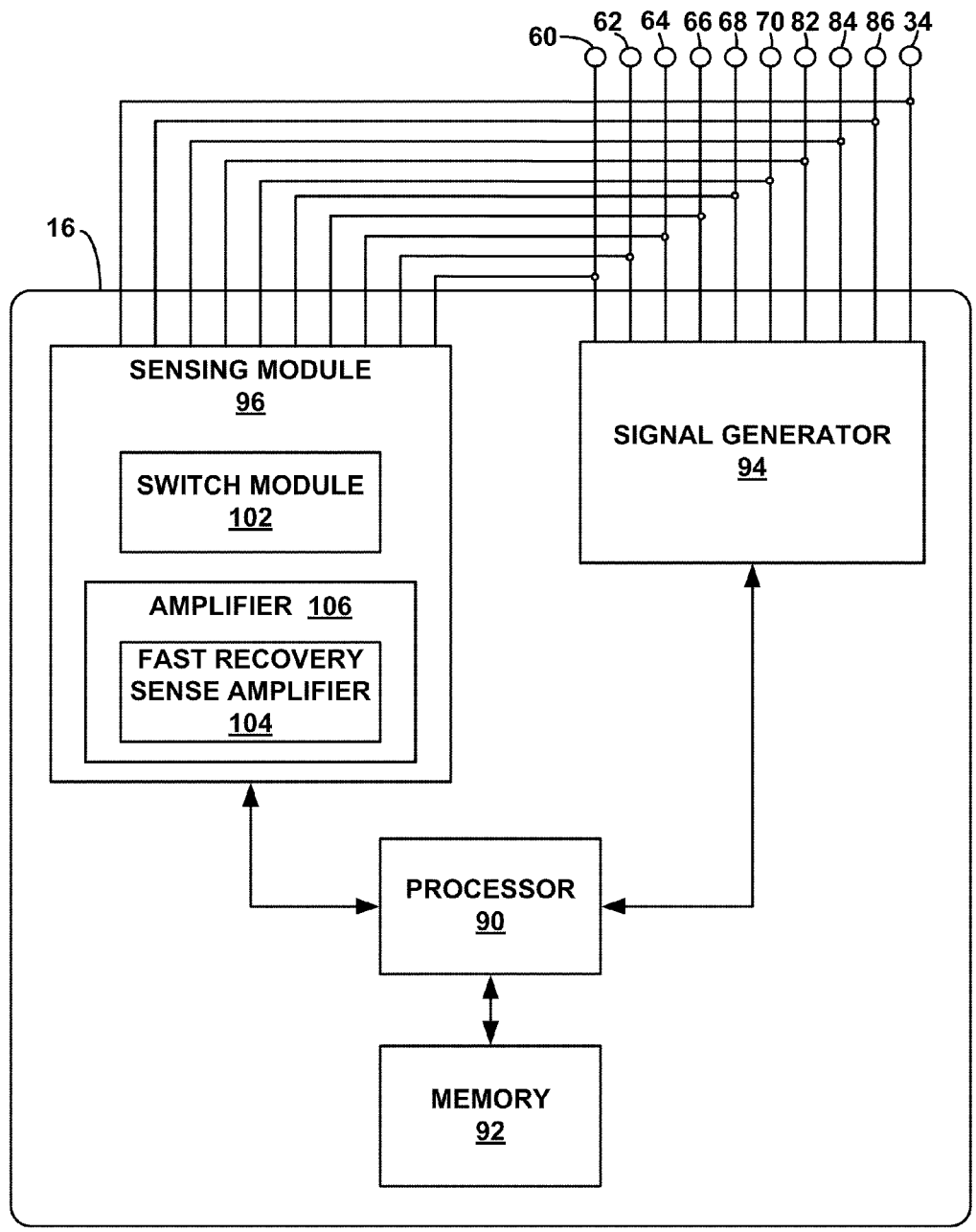
FIG. 5 is functional block diagram illustrating an example configuration of the ICD shown in FIG. 1.

FIG. 5 is a functional block diagram of one example configuration of ICD 16. In the illustrated example, ICD 16 includes a processor 90, memory 92, signal generator 94, and electrical sensing module 96. Memory 92 includes computer-readable instructions that, when executed by processor 90, cause ICD 16 and any other component of ICD 16 to perform various functions attributed to them herein. Memory 92 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Processor 90 may include any one or more of a microprocessor, a controller, a digital signal processor (DSP), an application specific integrated circuit (ASIC), a field-programmable gate array (FPGA), or equivalent discrete or integrated logic circuitry. In some examples, processor 90 may include multiple components, such as any combination of one or more microprocessors, one or more controllers, one or more DSPs, one or more ASICs, or one or more FPGAs, as well as other discrete or integrated logic circuitry. The functions attributed to processor 90 herein may be embodied as software, firmware, hardware or any combination thereof.

Processor 90 controls signal generator 94 to deliver stimulation therapy, e.g., pacing, cardioversion, or defibrillation, to heart 12 based on a selected one or more of therapy programs, which may be stored in memory 92. Signal generator 94 is electrically coupled to electrodes 60, 62, 64, 66, 68, 70, 82, 84, and 86, e.g., via conductors of the respective lead 18, 20, 22, or, in the case of housing electrode 34, via an electrical conductor disposed within housing 88 of ICD 16. A switch matrix may also be provided to connect signal generator 94 to a selected one or more of electrodes 34, 60, 62, 64, 66, 68, 70, 82, 84, and 86, and to cause the electrodes to have a selected polarity. Signal generator 94 delivers stimulation in the form pulses, or signals other than pulses, such as sine waves, square waves, or other substantially continuous time signals.

Electrical sensing module 96 monitors signals from at least one of electrodes 34, 60, 62, 64, 66, 68, 70, 82, 84 or 86 in order to monitor electrical activity of heart 12. As shown in FIG. 5, sensing module 96 includes a switch module 102 and an amplifier 106. Amplifier 106 is illustrated in FIG. 5 as comprising a fast recovery sense amplifier 104. As will be described in greater detail in this disclosure with respect to the circuit diagrams provided in FIGS. 6-10, fast recovery sense amplifier 104 may be one stage of multiple stages of amplifier 106. Amplifier 106 may, for example, also include one or more other gain stages or filtering stages in addition to fast recovery sense amplifier 104. Switch module 102 may be controlled by processor 90 for selecting which of the available electrodes are used to sense the heart activity, e.g., is coupled to amplifier 106.

Fast recovery sense amplifier 104 is a sense amplifier that uses a feedback network to clamp the input voltage to the gain amplifier to achieve fast recovery times as described in this disclosure. Amplifier 106 may also include one or more of a gain amplifier and a filter circuit for further increasing the signal-to-noise ratio (SNR) of the output of fast recovery sense amplifier 104 prior to processing the signal to monitor heart activity.

In some examples, sensing module 96 includes a plurality of sensing channels, each of which may comprise a fast recovery sense amplifier. Thus, fast recovery sense amplifier 104 may represent a plurality of fast recovery sense amplifiers where each of the plurality of sense amplifiers is dedicated to one of the sensing channels.

In some examples, one channel of sensing module 96 comprises an R-wave amplifier that receives signals from electrodes 60 and 62, which are used for pacing and sensing in right ventricle 28 of heart 12. Another channel comprises another R-wave amplifier that receives signals from electrodes 64 and 66, which are used for pacing and sensing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, one channel of sensing module 96 comprises a P-wave amplifier that receives signals from electrodes 68 and 70, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 96 may be selectively coupled to housing electrode 34, or elongated electrodes 82, 84, or 86, with or instead of one or more of electrodes 60, 62, 64, 66, 68 or 70, e.g., for unipolar sensing of R-waves or P-waves in any of chambers 26, 28, 36, or 32 of heart 12.

In some examples, sensing module 96 includes a channel that comprises an amplifier with a relatively wider pass band than the R-wave or P-wave amplifiers. The wide-band amplifier may comprise fast response sense amplifier 104. Signals from the selected sensing electrodes that are selected for coupling to this wide-band amplifier may be provided to a multiplexer, and thereafter converted to multi-bit digital signals by an analog-to-digital converter for storage in memory 92, or communication to a programmer or other external device, as an electrogram (EGM). Processor 90 may also employ digital signal analysis techniques to characterize the digitized signals to detect and classify the patient's heart rhythm from the electrical signals. Processor 90 may detect and classify the patient's heart rhythm by employing any of the numerous signal processing methodologies known in the art.

Figure 6:
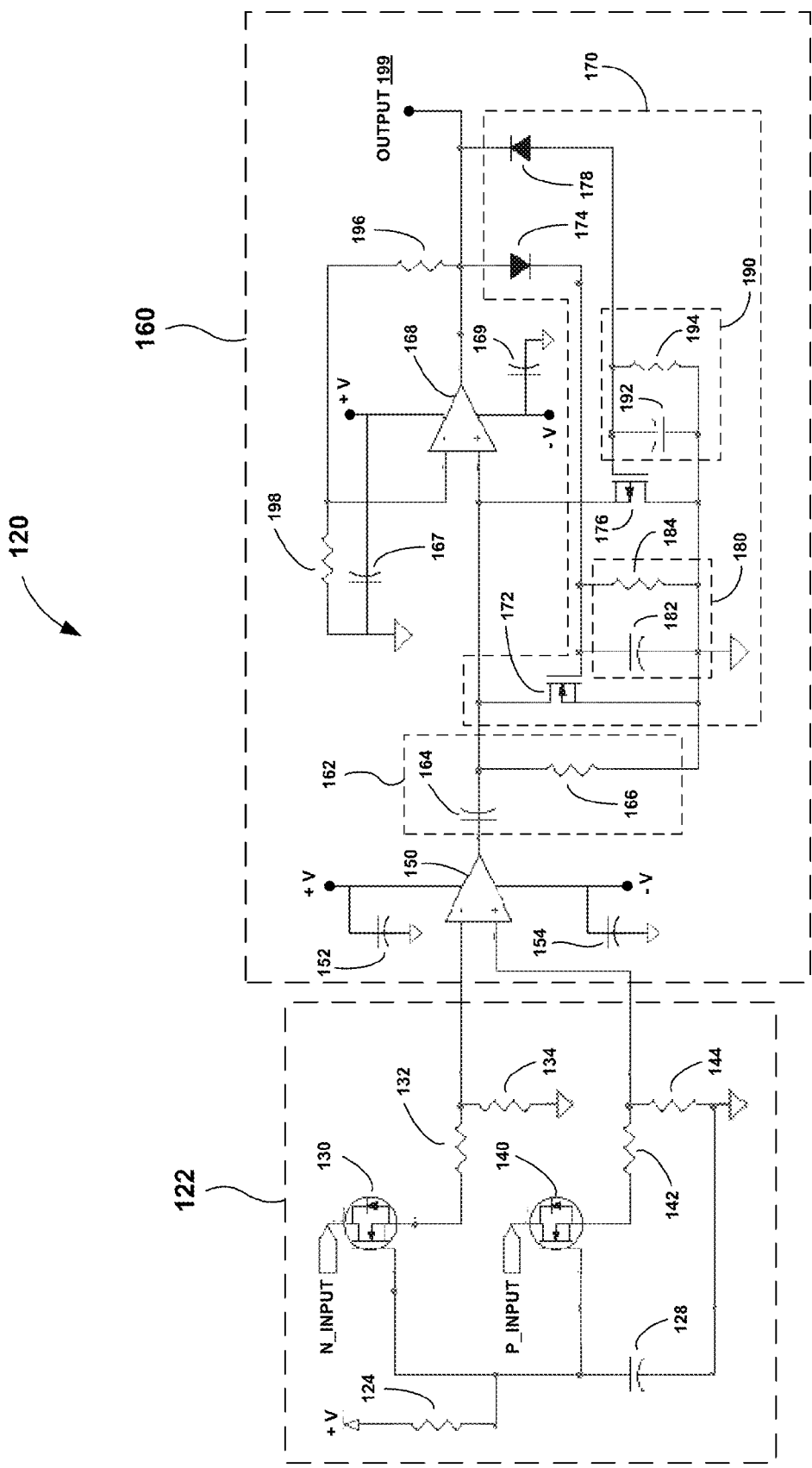
FIGS. 6-10 are schematic circuit diagrams illustrating example fast recovery signal conditioning physiological amplifiers.

FIG. 6 is a schematic circuit diagram illustrating an example circuit 120, which is an example implementation of fast recovery sense amplifier 104 in FIG. 5. Circuit 120 may be used for one or more of the multiple sensing channels of ICD 16. As previously described, fast recovery sense amplifier 104 is a signal conditioning physiological sense amplifier that uses a pole shifting technique to achieve a fast recovery time without blanking. In the example shown in FIG. 6, circuit 120 includes a front end 122 of the circuit that protects a back end 160 of the circuit from high voltages. Generally, the circuit components of back end 160 implement the pole shifting technique and may have a low voltage rating. Thus, front end 122 is configured to prevent back end 160 from being exposed to potentially harmful voltages produced by pacing, cardioversion, or defibrillation pulses. In particular, front end 122 automatically protects back end 160.

In FIG. 6, the inputs of circuit 120, i.e., P_INPUT and N_INPUT, are coupled, although not necessarily directly coupled, to sense electrodes. For example, P_INPUT may be coupled to a ring electrode and N_INPUT may be coupled to a tip electrode. As previously described, the voltage across these inputs may be less than approximately 20 mV for electrical cardiac signals or up to a few hundred volts for an externally applied defibrillation pulse. The differential voltage across the inputs of circuit 120 is applied to transistors 130 and 140. As described in greater detail below, transistors 130 and 140 are coupled to each other and to respective inputs of instrumentation amplifier 150 through resistors 132, 134, 142, and 144. Transistors 130 and 140 and resistors 132, 134, 142, and 144 form front end 122. Resistor 124 and capacitor 128 are also part of front end 122. Front end 122 blocks potentially harmful voltages from damaging back end 160 and, more particularly, instrumentation amplifier 150. Instrumentation amplifier 150 generates single ended signal based on the differential signal at its inputs. A discrete implementation of instrumentation amplifier 150 is not provided in FIG. 6, 7, 9, or 10 for the purpose of simplifying the circuit diagrams. However, a circuit diagram for a fast recovery sense amplifier that includes a discrete implementation of an instrumentation amplifier is provided in FIG. 8.

In FIG. 6, transistors 130 and 140 are N-channel enhancement mode metal oxide semiconductor field effect transistors (MOSFETs). In this disclosure, the term "transistors" is used to refer to MOSFETs. Although this disclosure references MOSFETs, it should be understood that other types of FETs or transistors may be used in place of the described MOSFETs as known to those skilled in the art of electrical circuits. The gate terminal for each of transistors 130 and 140 is coupled to a positive supply voltage (+V) through resistor 124. In an implantable device, such as an implantable cardioverter, implantable defibrillator, or purely diagnostic device, the supply voltage may be an approximately 5V rail voltage. However, it should be understood that other supply voltages, e.g., 6V or 12V, may be used. Other configurations for controlling the gate voltage of transistors 130 and 140 are possible, such as a voltage divider. Capacitor 128 is used to hold the voltage at the gate of transistors 130 and 140 substantially constant by supplying additional voltage stability if the power source experiences transient changes in voltage. The drain of each of transistors 130 and 140 is coupled to the respective input (N_INPUT or P_INPUT) and the source of each of transistors 130 and 140 is coupled a corresponding input of instrumentation amplifier 150 through resistors 132 and 142, respectively. The source of transistor 130 is coupled to the inverting input of instrumentation amplifier 150 through resistor 132 and the source of transistor 140 is coupled to the noninverting input of instrumentation amplifier 150 through resistor 142. Resistors 134 and 144 are coupled at one end to respective inputs of instrumentation amplifier 150 and to a system ground at the other end to provide a current path for amplifier 150 bias currents and also couples transistors 130 and 140 to each other.

Generally, transistors 130 and 140 are configured to operate as clamping devices to block high voltages from damaging components of back end 160. In particular, transistors 130 and 140 are biased such that the transistors operate in an analog pass mode that allows back end 160 to amplify the relatively small electrical cardiac signals when such small voltage signals are presented to N_INPUT and P_INPUT. Transistors 130 and 140 also operate in a linear voltage blocking mode for protecting back end 160 from high voltages between N_INPUT and P_INPUT, when high voltages are presented to the inputs. When operating in the voltage blocking mode, front end 122 clamps the input voltage to back end 160 and, more particularly, to instrumentation amplifier 150, at a predetermined value thereby protecting all the components of back end 160 from potentially harmful voltage levels. Although front end 122 clamps the input voltage to instrumentation amplifier 150, front end 122 is generally referred to as being configured to "block voltage" to protect back end 160 or as "voltage blocking circuitry" in order to avoid confusion with the voltage clamping performed by back end 160.

As one example, the gate voltage of transistors 130 and 140 may be controlled to be held at approximately 6 V relative to circuit reference. Transistor 140 may then operate in a linear voltage blocking mode when the source voltage for transistor 140 increases so that the gate-to-source threshold voltage is no longer satisfied for transistor 140, such as when a therapy pulse (pacing, cardioversion, or defibrillation pulse) is applied with sufficient amplitude and a polarity positive relative to P_INPUT and negative relative to N_INPUT. During application of such a therapy pulse, current flows though transistor 130 and subsequently though resistors 132, 134, 144, 142, and through transistor 140 thereby developing a voltage at the source of transistor 140 via the voltage across resistors 142 and 144 relative to circuit reference. When the source voltage of transistor 140 increases so that the difference between the gate voltage of approximately 6 volts and the source voltage of approximately 2.5 V no longer exceeds the gate-to-source threshold voltage of approximately 3.5 V, transistor 140 operates in a linear voltage blocking mode. When operating in a linear voltage blocking mode, transistor 140 creates a voltage drop between the source and drain terminals of transistor 140 to satisfy the gate-to-source threshold voltage. Consequently, a substantially constant voltage of approximately 2.5 V is present at the source of transistor 140 relative to circuit reference until the therapy pulse amplitude no longer drives transistor 140 into the linear voltage blocking mode, and thereby protects the non-inverting input of instrumentation amplifier 150 from a potentially damaging high voltage. Subsequently the inverting input of instrumentation amplifier 150 is protected from negative high voltage relative to circuit reference by the voltage drop present across resistor 134 as a relation to the amount of current flowing through transistors 130 and 140 and resistors 132, 134, 144, and 142. Although the voltage blocking capabilities of front end 122 are described with respect to an applied positive therapy pulse, front end 122 works in a similar fashion when a negative polarity therapy pulse is applied to circuit 120, i.e., transistor 130 operates in a linear voltage blocking mode and transistor 140 conducts a small current through its body diode.

Because transistors 130, 140 allow only 2.5 V when operating in a linear voltage blocking mode, resistors 132, 134, 142 and 144 can be chosen to limit the total current shunted and circuit 120 does not take a substantial amount of energy away from the patient. As an example, resistors 132 and 142 may be selected as 4.99 kΩ resistors and resistors 134 and 144 may be selected as 4.99 MΩ resistors. Additionally, because transistors 130, 140 are high voltage components circuit 120 may provide increased reliability over circuits that use transient voltage suppressors to block high voltages from the low voltage components of a sense amplifier. Transistors 130, 140 may be, as but one example, 1200 V components.

It is important to note that resistor 124 is merely an example and serves to illustrate one of many different biasing schemes for controlling the gate voltage of transistors 130 and 140. Similarly, resistors 132, 134 and resistors 142, 144 are merely examples and serve to illustrate one of many different biasing schemes for controlling the signal voltage at the inputs to instrumentation amplifier 150. Resistors 132, 134, 142, and 144, may be matched to each other, and the values of these resistors may be selected based on a desired maximum output voltage of instrumentation amplifier 150, i.e., a desired maximum for voltages presented to back end 160.

Back end 160 of circuit 120 operates as a sense amplifier for amplifying the signal at the output of instrumentation amplifier 150 in order to increase the SNR for improved signal processing. Back end 160 comprises instrumentation amplifier 150, a high pass filter 162, gain amplifier 168, and feedback network 170. High pass filter 162 includes capacitor 164 coupled in series with resistor 166. Capacitor 164 and resistor 166 may be selected such that high pass filter 162 has a relatively low cutoff frequency, e.g., 0.159 Hz, for filtering DC signals from gain amplifier 168. As an example, capacitor 164 may be a 1.0 µF capacitor and resistor 166 may be a 1 MΩ resistor. As shown in FIG. 6, gain amplifier 168 may be an operation amplifier configured to operate as a noninverting amplifier by applying negative feedback to the inverting input of gain amplifier 168 through resistors 196 and 198. Gain amplifier 168 may also be configured to operate as an inverting amplifier.

Instrumentation amplifier 150 and gain amplifier 168 receive power from a positive voltage source (+V) and a negative voltage source (−V). The voltage sources may be positive and negative voltage rails for the device, e.g., IMD 16. The value for the voltage sources generally depends on its power requirements and may have a value of, for example, 3 V, 5V, or 12V Capacitors 152, 154, 167, and 169 serve a similar purpose as capacitor 128, i.e., are used to hold the supply voltage substantially constant by providing additional voltage stability if the power source experiences transient changes in voltage.

Feedback network 170 includes a positive feedback path comprising transistor 172 and diode 174, and a negative feedback path comprising transistor 176 and diode 178. Transistor 172 may be implemented as an N channel enhancement mode MOSFET and transistor 176 may be implemented as a P channel enhancement mode MOSFET. In FIG. 6, feedback network 170 also includes time delay units 180 and 190. Diodes 174 and 178 are used to prevent any signal from time delay units 180 and 190 from affecting output 199 when there is a polarity swing in output 199. Time delay unit 180 includes capacitor 182 and resistor 184. Time delay unit 190 includes capacitor 192 and 194. The values of the capacitors and resistors for time delay units 180 and 190 may be selected to prevent incorrect level sensing, as described below. For example, capacitors 182 and 192 may be 0.1° F. capacitors and resistors 184 and 194 may be 1 MΩ resistors.

Figure 7:
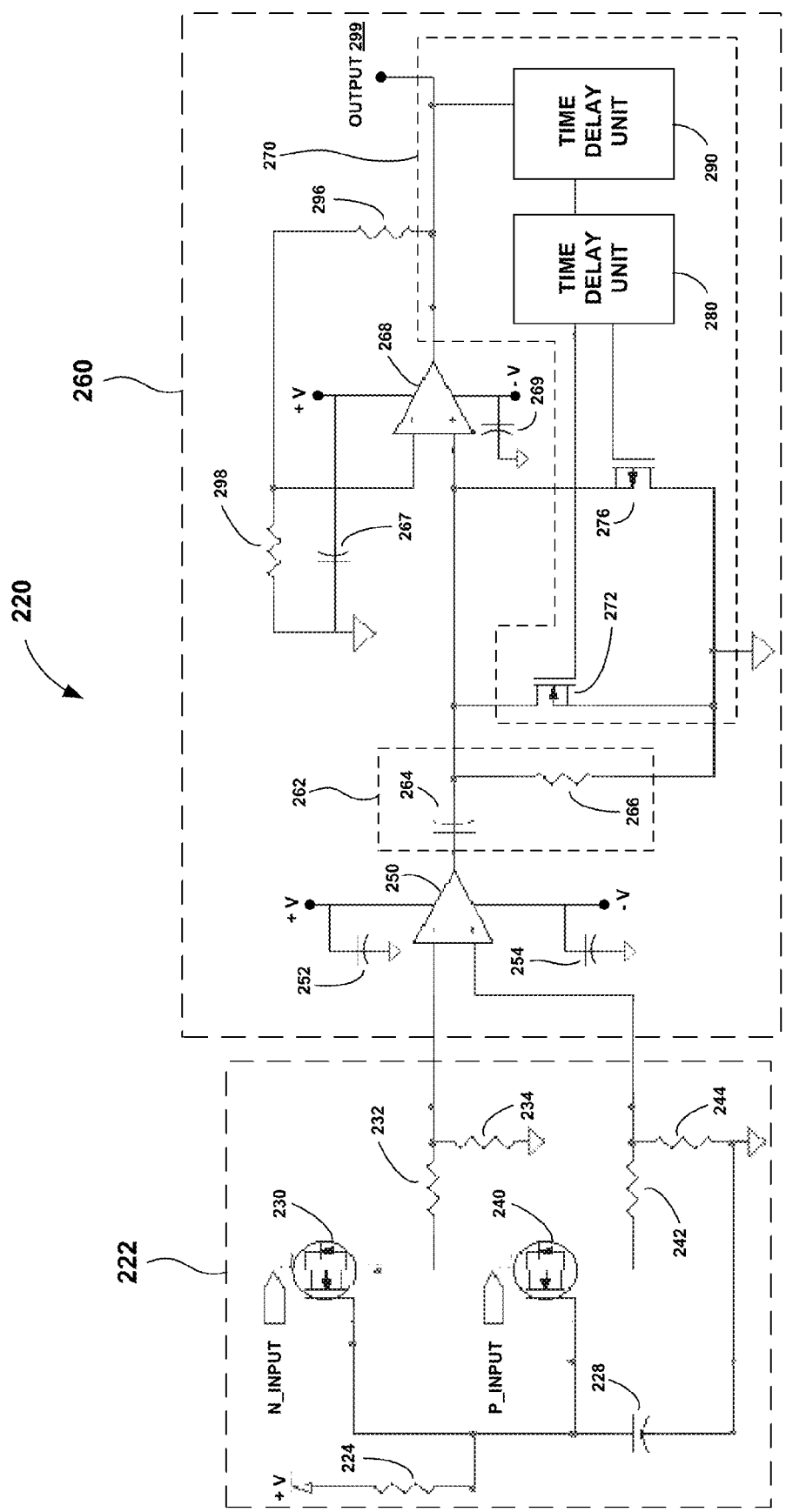

Although time delay units 180 and 190 are shown in FIG. 6 as a resistor and capacitor coupled in parallel between a corresponding feedback path and a system ground, time delay units may be implemented using other analog or digital components. Another example for implementing time delay units is shown in FIG. 7.

Similar to front end 122, back end 160 also operates in two modes. Back end 160 automatically switches between the two different modes of operation based on the input voltage to gain amplifier 168. In particular, back end 160 is configured such that when the input voltage to gain amplifier 168 is less than a predetermined threshold value, back end 160 operates in a first mode (sense amplifier mode), and operates in a second mode (fast recovery mode) when the threshold voltage is exceeded. Again, the threshold voltage may be selected to be a value that is greater than a typical sensed electrical cardiac signal and less than a typical therapy pulse. The predetermined threshold value is a function of the gain of amplifier 168 and the gate-to-source threshold values for transistors 172 and 176. An example threshold value may be within a range of approximately 20 mV to approximately 500 mV, and may be selected as approximately 420 mV. As will be described in greater detail below, the gain of amplifier 168 may also be selected based on the predetermined threshold value. Thus, the value of resistors 196 and 198 may be selected since resistors 196 and 198 set the gain of amplifier 168.

In a first mode, back end 160 operates as a sense amplifier that generates output 199 as an amplified version of the input voltage to gain amplifier 168. When operating in the sense amplifier mode, feedback network 170 is not turned on, i.e., does not effectively apply a feedback signal that changes output 199. Accordingly, the output of instrumentation amplifier 150 is filtered by high pass filter 162. High pass filter 162 suppresses signal frequencies below the cutoff frequency. For circuit 120, high pass filter 162 may be configured to suppress direct current signals and, thus, have a cutoff frequency of less than approximately 1 Hz.

Gain amplifier 168 amplifies the filtered signal to generate output 199. In some examples, such as when the gain of gain amplifier 168 is approximately 10 or less, output 199 may be applied to another gain and/or filter amplifier to further increase the SNR prior to processing the signal. The reason that output 199 may be applied to a second gain amplifier is that output 199 is applied as feedback to transistors 172 and 176 to control when the transistors are on (conducting) and off (non-conducting) via feedback network 170 as described below.

Back end 160 may operate in the second mode (fast recovery mode) when, for example, the input voltage to gain amplifier 168 exceeds the predetermined threshold voltage. The predetermined threshold voltage may be determined by transistors 172 and 176. This is because transistors 172 and 176 turn on when the respective gate voltage exceeds the transistor on threshold voltage. For transistors 172 and 176 the transistor threshold voltage is approximately +3.5 and −3.5 V respectively for the purpose of describing circuit 120. Because there is also approximately a 0.7 V drop through diodes 174 and 178, transistors 172 and 176 turn on when output 199 exceeds approximately ±4.2 V. Because cardiac signals may have an amplitude of approximately 20 mV or less and a therapy pulse may have an amplitude of approximately 1 V or more, the gain of amplifier 168 may be selected such that a signal with an amplitude between these two values causes the predetermined threshold value to be exceeded. Thus, gain amplifier 168 may be configured with a gain of approximately 10 thereby resulting in an input threshold voltage of approximately 420 mV. Although other gain values are possible, circuit 120 will be described according to this example.

Because the gain of amplifier 168 is set by the value of resistors 196 and 198, resistor 196 may be selected to be a 9 kΩ resistor and resistor 198 may be selected as a 1 kΩ resistor. It is important to note that other threshold voltage values are possible. For example, the threshold value may be different in an example in which diodes with an operational voltage drop of 0.3 V are used in place of diodes 174 and 178.

With respect to the described example, when the input voltage of gain amplifier 168 exceeds approximately 420 mV, the gate voltage at transistor 172 turns transistor 172 on and feedback network 170 provides a low resistance current path through transistor 172 that connects capacitor 164 to a system ground. In operation, a small amount of current may flow through resistor 166, but a substantial amount of current may flow through transistor 172 since the resistance of transistor 172 may be much less than that of resistor 166. This allows the charge on capacitor 164 to quickly develop during the therapy pulse and quickly drain when transistor 172 is turned on thereby providing for the fast recovery time of circuit 120. Back end 160 is described as using a pole shifting technique because the lower resistance current path provided by transistor 172 when the transistor is turned on effectively upshifts the pole of the high pass filter. As an example, high pass filter 162 may shift from an approximately 0.15 Hz high pass filter to an approximately 1 MHz high pass filter.

In FIG. 6, transistor 172 does not turn on immediately after the therapy pulse is sensed. Instead, transistor 172 turns on after a short period of time, i.e., shorter than the duration of the therapy pulse, due to propagation of the signal (therapy pulse) through gain amplifier 168 and charging of capacitor 182. When transistor 172 turns on, the charge on capacitor 164 quickly drains to ground through the low resistance path provided by transistor 172 thereby driving the input voltage to gain amplifier 168 to approximately 0 V.

Transistor 172 also does not turn off immediately after the charge on capacitor 164 is drained. Rather, the charge built up on capacitor 182 while diode 172 is conducting keeps transistor 172 turned on. This is because the charge on capacitor 182 is bled off through resistor 184 and leakage current through transistor 172 since diode 174 prevents current from flowing in the opposite direction. Accordingly, the input voltage to gain amplifier 168 is clamped at approximately 0 V during the time delay. By keeping transistor 172 turned on for the duration of the time delay, any signal is shunted through transistor 172 and the input voltage remains clamped at approximately 0 V until capacitor 182 discharges below the on threshold of transistor 172.

Clamping the input voltage at approximately 0 V for the duration of the time delay prevents incorrect level sensing by subsequent processing circuitry. Tissue surrounding electrodes used for sensing may become polarized following delivery of a therapy pulse. If polarization is present and the input voltage is not clamped to approximately 0 V, then the subsequent signal processing may incorrectly interpret the DC polarization to be an electrical cardiac event. For this reason, it is important for the time delay to extend for a period of time following the end of the therapy pulse, e.g., until the DC polarization dissipates. In FIG. 6, the time delay may be controlled by the selection of capacitor 182 and resistor 184.

The negative feedback path that includes transistor 176, diode 178, and time delay unit 190 operates in a manner similar to that for the previously described positive feedback path when a negative voltage that exceeds the predetermined threshold value at the input to gain amplifier 168.

FIG. 7 is a schematic circuit diagram illustrating another example circuit 220 that may be used to implement fast recovery amplifier 104 in FIG. 5. In general, circuit 220 operates in a similar manner as circuit 120 shown in FIG. 6. Circuit 220, however, provides an alternate configuration for implementing a time delay in the feedback network.

Accordingly, elements of circuit 220 have reference labels that corresponding to similar operating elements of circuit 120. That is, front end 222 that includes resistors 224, 232, 234, 242, and 244, capacitor 228, and transistors 230 and 240 operate in a similar manner as front end 122 that includes resistors 124, 132, 134, 142, and 144, capacitor 128, and transistors 130 and 140. Additionally, back end 260 includes instrumentation amplifier 250, high pass filter 262 comprising capacitor 264 and resistor 266, a noninverting gain amplifier comprising gain amplifier 268 and resistors 296 and 298, and capacitors 252, 254, 267, and 269 that correspond to and operate similar to back end 160 that includes instrumentation amplifier 250, high pass filter 162 comprising capacitor 164 and resistor 166, a noninverting gain amplifier comprising gain amplifier 168 and resistors 196 and 198, and capacitors 152, 154, 167, and 169 of circuit 120 in FIG. 6. With respect to feedback network 170 of circuit 120, feedback network 270 of circuit 220 operates in the same way. Feedback network 270, however, includes time delay units 280 and 290 that may have alternate configurations to those of time delay units 180 and 190 in circuit 120. In any case, transistors 272 and 276 of circuit 220 operate in the same manner as transistors 172 and 176 of circuit 170.

For example, time delay units 280 and 290 may be configured as a time delay multivibrator, or a digital time delay that is triggered when output 299 is greater than a threshold value. A digital time delay may be implemented by applying output 299 to an FPGA, DSP, or other processing circuitry of processor 90 in FIG. 5.

Figure 8:
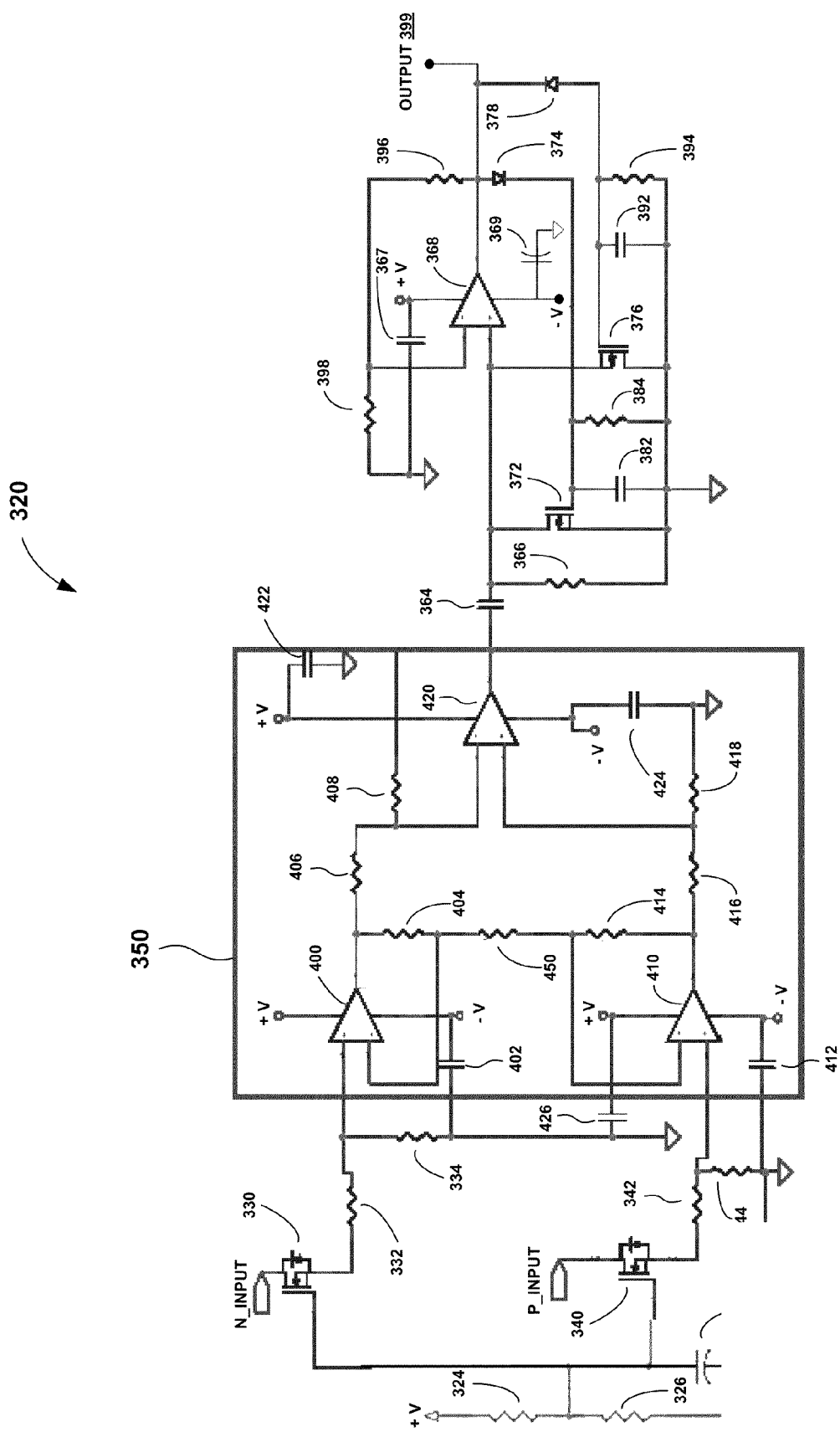

FIG. 8 is a schematic diagram illustrating an additional example circuit 320 that is an example implementation of fast recovery sense amplifier 104 in FIG. 5. In general, circuit 320 operates in a similar manner as circuit 120 as shown in FIG. 6, but provides a discrete implementation of an instrumentation amplifier. Circuit 320 also provides another example configuration for controlling the gate voltage of voltage blocking transistors 330 and 340.

Accordingly, elements of circuit 320 that have reference labels correspond to similar operating elements of circuit 120. That is, front end 322 that includes resistors 332, 334, 342, and 344, capacitor 328, and transistors 330 and 340 operate in a similar manner as front end 122 that includes resistors 132, 134, 142, and 144, capacitor 128, and transistors 130 and 140. Circuit 320, however, includes resistors 324 and 326 configured as a voltage divider for controlling the gate voltage of transistors 330 and 340, respectively. For example, resistors 324 and 326 may be matched to each other so that the voltage supplied by the power source (+V) is equally distributed to transistors 330 and 340.

Additionally, back end 360 that includes instrumentation amplifier 350, high pass filter 362 comprising capacitor 364 and resistor 366, a noninverting gain amplifier comprising gain amplifier 368 and resistors 396 and 398, and capacitors 367 and 369 correspond to and operate similar to back end 160 that includes instrumentation amplifier 150, high pass filter 162 comprising capacitor 164 and resistor 166, a noninverting gain amplifier comprising gain amplifier 168 and resistors 196 and 198, and capacitors 167 and 169 of circuit 120 in FIG. 6. However, FIG. 8 shows an example discrete implementation of instrumentation amplifier 350 that includes operational amplifiers 400, 410, and 420, resistors 402, 404, 406 408, 412, 414, 416, and 418, and capacitors 422, 424, and 426. With respect to the feedback network of circuit 320, the feedback network includes transistors 372 and 374, diodes 374 and 378, capacitors 382 and 392, and resistors 384 and 394 that operate similar to transistors 172 and 174, diodes 174 and 178, capacitors 182 and 192, and resistors 184 and 194. It should be understood that circuit 320 includes a feedback network and time delay units similar to feedback network 170 and time delay units 180 and 190 of circuit 120.

Figure 9:
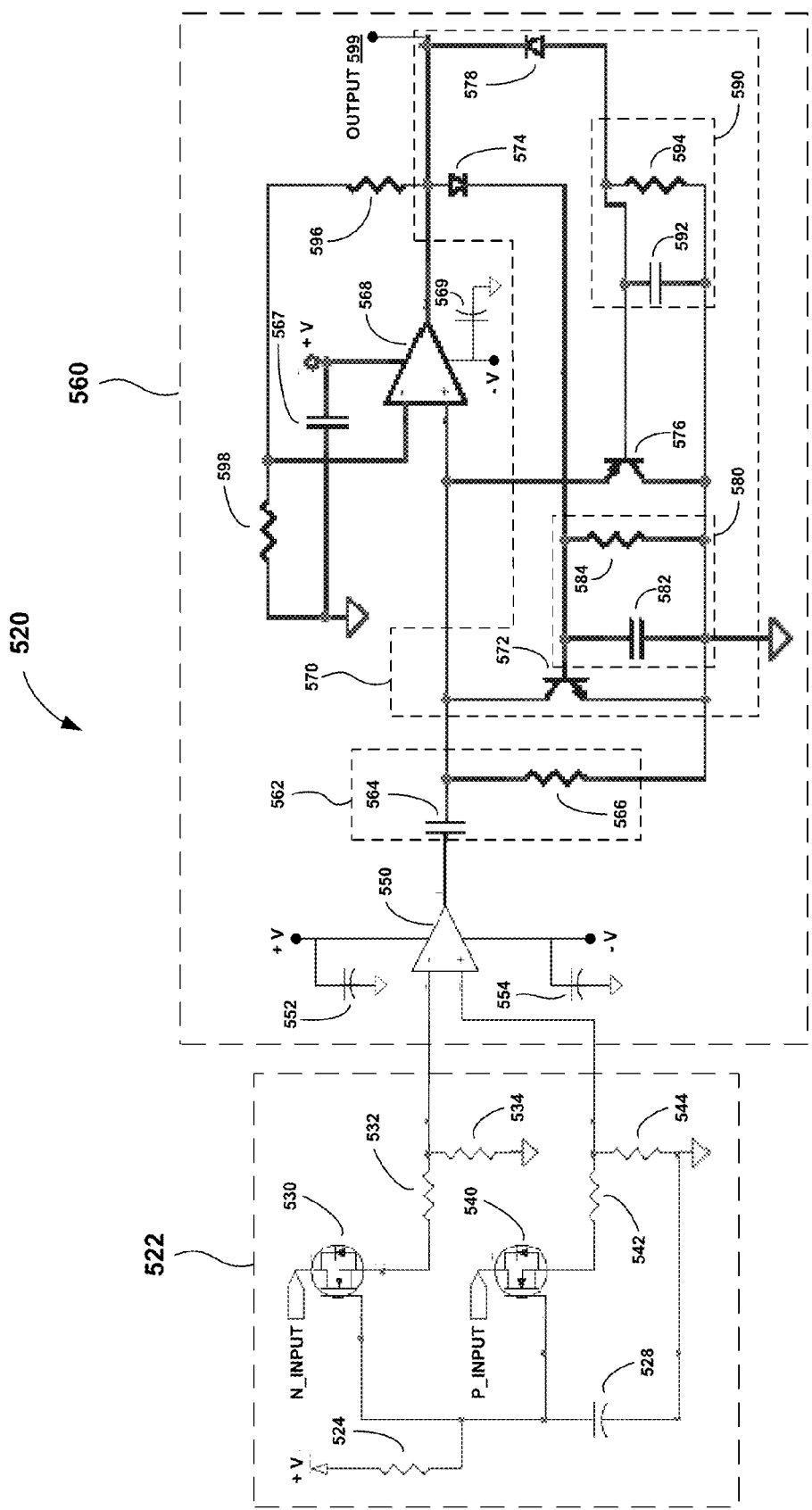

FIG. 9 is a schematic diagram illustrating another example circuit 520 that is another example implementation of fast recovery amplifier 104 in FIG. 5. In general, circuit 520 operates similar to circuit 120 shown in FIG. 6. Circuit 520, however, uses bipolar junction transistors (BJTs), e.g., NPN or PNP transistors, instead of the MOSFETs which were used for circuit 120.

Accordingly, elements of circuit 520 have reference labels that corresponding to similar operating elements of circuit 120. That is, front end 522 that includes resistors 524, 532, 534, 542, and 544, capacitor 528, and transistors 530 and 540 operate in a similar manner as front end 122 that includes resistors 124, 132, 134, 142, and 144, capacitor 128, and transistors 130 and 140. Additionally, back end 560 that includes instrumentation amplifier 550, high pass filter 562 comprising capacitor 564 and resistor 566, a noninverting gain amplifier comprising gain amplifier 568 and resistors 596 and 598, capacitors 552, 554, 567, and 569, feedback network 570 that includes transistors 572 and 576, and diodes 574 and 578, and time delay units 580 and 590 that include capacitors 582 and 592 and resistors 584 and 594 correspond to back end 160 that includes instrumentation amplifier 150, high pass filter 162 comprising capacitor 164 and resistor 166, a noninverting gain amplifier comprising gain amplifier 168 and resistors 196 and 198, capacitors 152, 154, 167, and 169, feedback network 170 that includes transistors 172 and 176, and diodes 174 and 178, and time delay units 180 and 190 that include capacitors 182 and 192 and resistors 184 and 194.

FIG. 9 illustrates that fast recovery amplifiers according to this disclosure are not limited to examples that include MOSFETs, and may additionally or alternatively include other transistors, such as BJTs. Accordingly, where aspects of the disclosure are described herein with reference to MOSFETs, and utilizing the terminology associated with MOSFETs, it will be understood that those aspects may be implemented by a BJT or other transistor. The term transistor is used herein to refer to any type of transistor, including MOSFETs or BJTs.

Where terminology associated with MOSFETs is used herein, such as gate, source and drain, it will be understood that other corresponding terminology associated with other types of transistors, such as base, emitter and collector for BJTs, or more generally the control terminal, input terminal and output terminal, is also applicable. Thus, any reference herein to application of a voltage or signal to a drain may be considered to encompass application of the voltage or signal to an input terminal. Similarly, any reference herein to a gate-to-source voltage or threshold may be considered to encompass a base-to-emitter voltage or threshold, and may be referred to more generally as a control terminal to reference terminal voltage or threshold.

Figure 10:
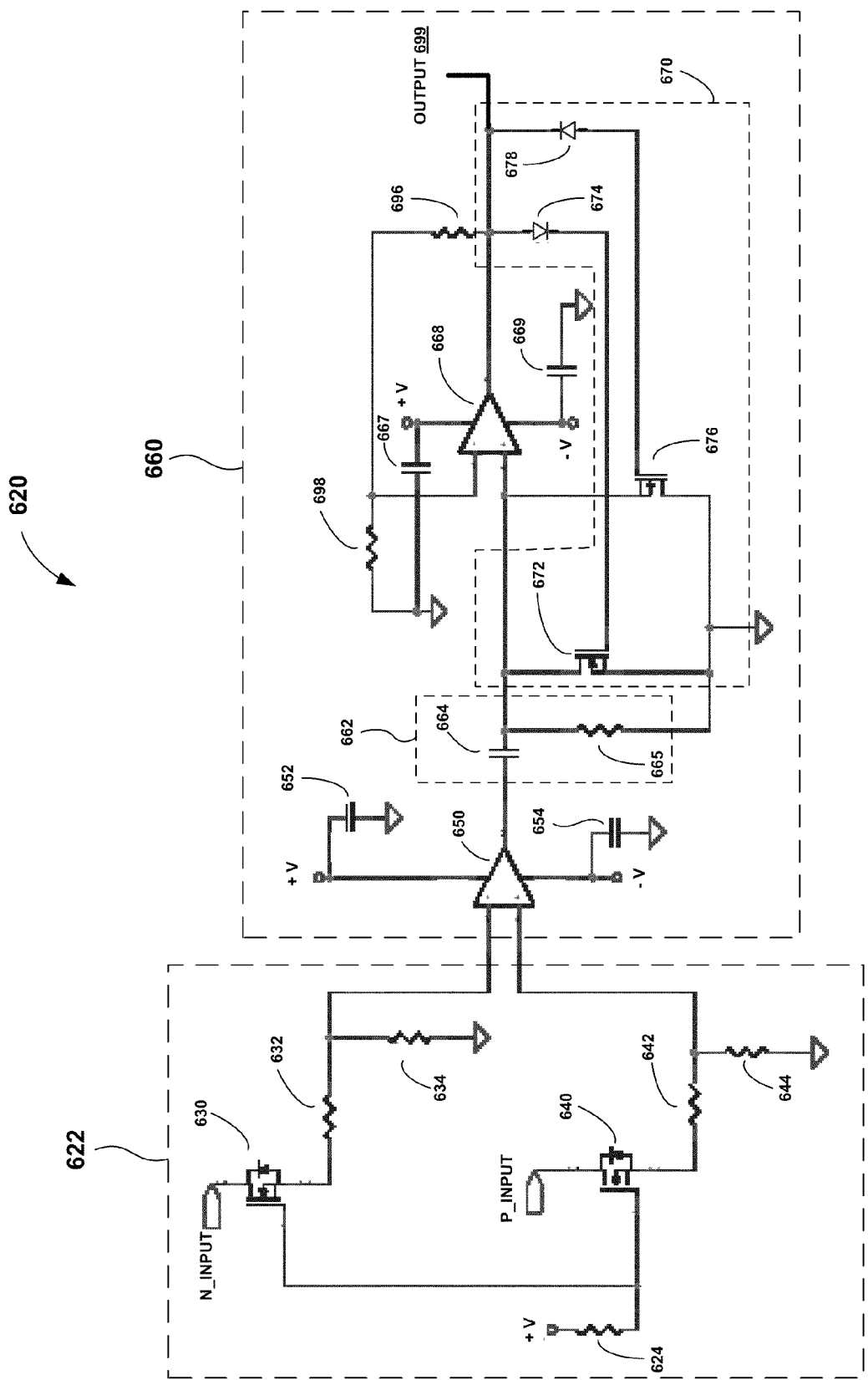

FIG. 10 is a schematic diagram illustrating another example circuit 620 that is another example implementation of fast recovery amplifier 104 in FIG. 5. Generally, circuit 620 operates similar to circuit 120 shown in FIG. 6, but does not include time delay units. Because circuit 620 does not include time delay units, the time response of the circuit is different and is described in greater detail below. A timing diagram for circuit 620 is shown in FIG. 11D.

Because circuit 620 operates similar to circuit 120, elements of circuit 620 have reference labels that correspond to similar operating elements of circuit 120. That is, front end 622 that includes resistors 624, 632, 634, 642, and 644, and transistors 630 and 640 operate in a similar manner as front end 122 that includes resistors 124, 126, 132, 134, 142, and 144, and transistors 130 and 140. Additionally, back end 660 that includes instrumentation amplifier 650, high pass filter 662 comprising capacitor 664 and resistor 665, a noninverting gain amplifier comprising gain amplifier 668, resistors 696 and 698, capacitors 652, 654, 667, and 669, and feedback network 670 that includes transistors 672 and 676, and diodes 674 and 678 correspond to back end 160 that includes instrumentation amplifier 150, high pass filter 162 comprising capacitor 164 and resistor 166, a noninverting gain amplifier comprising gain amplifier 168 and resistors 196 and 198, capacitors 152, 154, 167, and 169, and feedback network 170 that includes transistors 172 and 176, and diodes 174 and 178.

However, because circuit 620 does not include time delay units, the clamping feature of back end 660 works differently than that of circuits 120, 220, 320, and 520. In FIG. 10, transistor 672 turns on when the input voltage of gain amplifier 668 exceeds approximately 420 mV, thereby providing a low resistance current path to quickly drain the charge on capacitor 164. Accordingly, transistor 672 turns on when a therapy pulse is applied and clamps the input voltage at approximately 420 mV for the duration of the therapy pulse. When the therapy pulse ends, the charge on capacitor 672 drains through resistor 665.

Again, the negative feedback path that includes transistor 676 and diode 678 operates in a manner similar to that for the previously described positive feedback path when a negative voltage, e.g., negative therapy pulse, that exceeds the predetermined threshold value (420 mV with respect to circuit 620) at the input to gain amplifier 668.

FIGS. 11A-D are timing diagrams that illustrate a voltage signal over time at various measurement points of a fast recovery sense amplifier. For purposes of description, FIGS. 11A-C will be described with reference to circuit 120 shown in FIG. 6. FIG. 11D will be described with reference to circuit 620 shown in FIG. 10. It should be understood that the relative amplitudes in FIGS. 11A-D may not be scaled appropriately. However, the timing diagrams are synchronized in time to show the voltage at different points in the sense amplifier circuits at a given point in time.

Figure 11A:
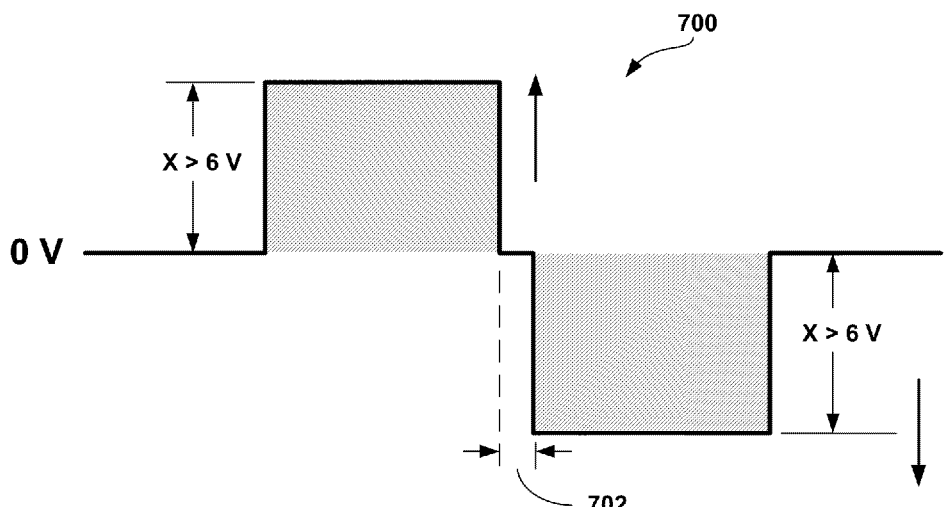
FIGS. 11A-D are timing diagrams illustrating example operation of a fast recovery signal conditioning physiological amplifier.

FIG. 11A is a timing diagram illustrating an input voltage signal 600 for circuit 120, although it should be understood that signal 700 may be an appropriate signal for any of circuits 120, 220, 320, 520, and 620. In particular, signal 700 in FIG. 11A is a square wave with a positive polarity pulse and negative polarity pulse. As shown in FIG. 11A, the positive and negative pulses may have an amplitude greater than approximately 1 V. Typically, a pacing pulse delivered by an ICD may have amplitude of approximately 1 V or more and a defibrillation pulse may have amplitude of up to 800 V or more. In any case, the purpose of signal 700 is to represent any therapy pulse amplitude that may be delivered to a patient regardless of waveform shape and, thereby presented to circuit 120. FIG. 11A also shows the positive and negative pulses of signal 700 separated by a time period 702 over which the signal has an amplitude of zero.

Figure 11B:
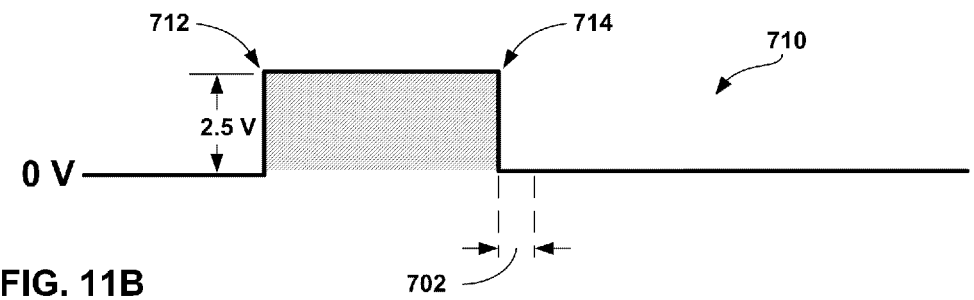

FIG. 11B is a timing diagram illustrating a voltage signal 710 at the source of transistor 140 relative to circuit ground of circuit 120 in FIG. 6. It should be understood, however, that the timing diagram in FIG. 11B is representative of the operation of each of circuits 120, 220, 320, 520, and 620, since all these circuits include a voltage blocking front end. The purpose of the timing diagram shown in FIG. 11B is to illustrate the operation of transistor 140 as a clamping device that blocks potentially harmful voltage levels from the back end of the sense amplifier circuit. With reference to input voltage signal 700, when the gate-to-source voltage of transistor 140 is no longer satisfied, transistor 140 clamps the voltage at its source at approximately 2.5 V relative to circuit ground. As previously described, the gate voltage of transistor 140 may be controlled to be approximately 6 V by connecting the gate of transistor 140 to a voltage rail through resistor through 124. Consequently, when input signal 700 exceeds 3.5 V, transistor 140 operates in a linear voltage blocking mode by creating a voltage drop across its source to drain to effectively clamp the source voltage at 2.5 V. Rising edge 712 of signal 710 shows transistor 140 clamping the voltage at its source at 2.5 V while input signal 700 remains greater than 6 V. The falling edge 714 of signal 710 coincides with the end of the positive pulse of signal 700.

During time period 702, both signal 700 and signal 710 have an amplitude of zero. Also, during the negative pulse of signal 700, signal 710 has a voltage of approximately 0 V. This is because the source of transistor 140 is slightly negative relative to circuit common due to the voltage drop created though resistors 142 and 144 and the reverse polarity of the pulse. Consequently, the negative pulse of signal 700 turns on transistor 140 so that it conducts resulting in almost no voltage drop between the source and drain terminals.

Figure 11C:
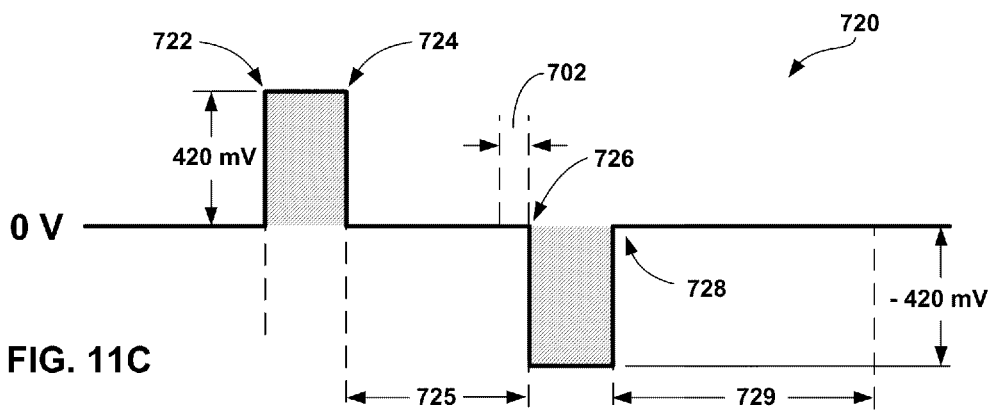
Figure 11D:
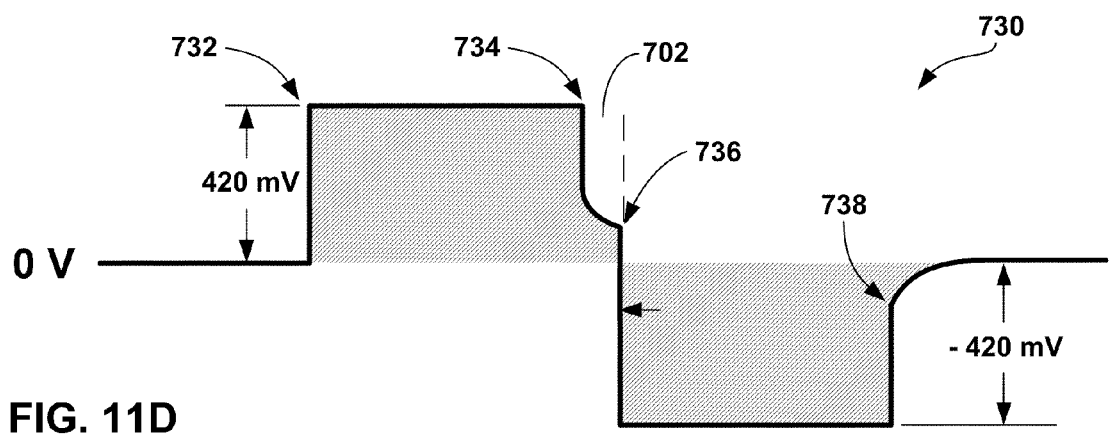

FIG. 11C is a timing diagram illustrating a voltage signal 720 at the input to gain amplifier 168 of circuit 120 in FIG. 6.

As shown in FIG. 11C, reference numeral 722 indicates when transistor 172 turns on at the beginning of the positive polarity pulse of signal 700. As previously described, transistor 172 may turn on when the input voltage to gain amplifier 168 exceeds approximately 420 mV and clamp the input voltage at that value while the signal builds charge on capacitor 182. This causes a voltage at the gate of transistor 172 that turns transistor 172 on while the charge on. Because transistor 172 is on, the charge on capacitor 164 quickly drains through transistor 172 thereby clamping the input voltage to gain amplifier 168 at approximately 0 V. With the input to amplifier 168 at zero volts the output of 168 also goes to zero volts and Diode 174 blocks current stored in capacitor 182 from returning to zero thereby keeping transistor 172 on after the output of amplifier 168 is below voltage necessary to keep transistor 172 on. Transistor 172 remains on while capacitor 182 dissipates through resistor 184 and through the gate leakage current of transistor 172. Reference numeral 724 indicates when the charge on capacitor 182 is sufficient to turn on transistor 172 and keeps transistor 172 turned on and the input voltage clamped to approximately 0 V for the duration of the time delay unit 180 or upon polarity reversal of the therapy pulse.

The input voltage remains clamped at approximately 0 V over the "time delay" 725, i.e., until the capacitor 182 discharges below the on threshold of transistor 172 or upon polarity reversal of the therapy pulse 726. In FIG. 11C, time delay unit 180 and, thus, capacitor 182 and resistor 184, are selected so that the time delay extends at least as long as time period 702. Generally, the time delay units 190 and 180 are of the same duration and are selected so that DC polarization of the tissue electrode interface following a therapy pulse does not cause false level sensing regardless of the polarity of the therapy pulse. That is, the time delay is selected so that the input voltage to gain amplifier 168 remains clamped at approximately 0 V until the DC polarization dissipates. In FIG. 11C, time delay 729 is not truncated by an additional therapy pulse and can extend to its full duration so that DC polarization that may temporarily reside at the tissue electrode interface does not lead to false level sensing.

As shown in FIG. 11C, circuit 120 and, more particularly, back end 160, operates in a similar manner when a negative therapy pulse is sensed. Reference numeral 726 indicates when the negative pulse of signal 700 begins and transistor 176 turns on to clamp the input voltage to gain amplifier 168 at approximately −420 mV. The input voltage remains clamped at this value until capacitor 192 is charged, indicated by reference numeral 728, and creates a voltage that keeps transistor 176 turned on. Thus, the input voltage clamps to approximately 0 V at reference numeral 728 and remains clamped at approximately 0 V for the time delay 729.

FIG. 11D is a timing diagram illustrating a voltage signal 730 at the input to gain amplifier 668 of circuit 620 in FIG. 10 when time delay units 180 and 190 are not present and voltage signal 700 of FIG. 11A is applied to circuit 620. As shown in FIG. 11D, reference numeral 732 indicates when transistor 672 turns on at the beginning of the positive polarity pulse of signal 700. As previously described, transistor 672 may turn on when the input voltage to gain amplifier 668 exceeds approximately 420 mV and clamps the input voltage at that value for the duration of the positive pulse of signal 700.

Transistor 672 turns off when the positive pulse of signal 700 ends, which is indicated by reference numeral 734. Although the amplitude of signal 700 is zero over time period 702 and transistor 172 is off, the exponential decaying signal of over time period 702 is the result of the high pass filter pole moving back to the original setting and charge moving back onto capacitor 664 much more slowly through resistor 665.

This charge on capacitor 664 decays exponentially until the charge is dissipated or the negative pulse of signal 700 begins.

When the negative pulse of signal 700 begins, which is marked by reference numeral 736, transistor 676 turns on and clamps in the input voltage to gain amplifier 668 at approximately −420 mV. Transistor 676 clamps the input voltage at this example value until the negative pulse of signal 700 ends, which is marked on signal 730 with reference numeral 738. Again, the input voltage at gain amplifier 668 decays exponentially after the end of the negative pulse of signal 700 due the filter pole moving back to the original value before clamping was enabled.

A number of examples have been described. These and other examples are within the scope of the following claims.

The invention claimed is:

1. A physiological sense amplifier configured for use in a medical device to sense a physiological electrical signal of a patient comprising:
   a high pass filter comprising a capacitor and a resistor coupled in series, wherein a voltage applied across the resistor is proportional to the physiological electrical signal;
   an amplifier that amplifies an input voltage to generate an output voltage, wherein the input voltage is a function of the voltage applied to the resistor when the input voltage is less than a predetermined threshold value; and
   a feedback network comprising a transistor coupled in parallel with the resistor,
wherein the output voltage of the amplifier is coupled to a control terminal of the transistor to activate the transistor when the input voltage exceeds the predetermined threshold value, and
wherein the transistor clamps the input voltage of the amplifier to a substantially constant value when the transistor is activated.

2. The sense amplifier of claim 1,
   wherein the input voltage exceeds the predetermined threshold value when therapeutic electrical stimulation is delivered to the body of the patient, and
   wherein the sense amplifier has a recovery time of less than approximately one millisecond following delivery of the electrical stimulation.

3. The sense amplifier of claim 2, wherein the electrical stimulation comprises at least one of a cardiac pacing pulse, a cardioversion pulse, defibrillation pulse, or other therapy pulse.

4. The sense amplifier of claim 1, wherein the physiological signal comprises a cardiac signal.

5. The sense amplifier of claim 1, wherein the predetermined threshold value is a function of a control terminal to input terminal threshold value of the transistor.

6. The sense amplifier of claim 1, wherein the clamped input voltage value is approximately zero Volts.

7. The sense amplifier of claim 1, wherein, when the transistor is activated a pole of the high pass filter is shifted.

8. The sense amplifier of claim 1, wherein, when the transistor provides a lower resistance current path for the capacitor to either discharge or charge when the transistor is activated to clamp the input voltage at the substantially constant value.

9. The sense amplifier of claim 1,
   wherein the feedback network comprise a time delay unit that applies a voltage to a control terminal of the transistor for a period of time after the transistor is activated, and
   wherein the voltage applied to the control terminal of the transistor by the time delay unit biases the transistor to provide the lower resistance current path for the capacitor to either discharge or charge the capacitor for the period of time.

10. The sense amplifier of claim 9, wherein the period of time ends at a time after the input voltage that exceeds the predetermined threshold value has ended.

11. The sense amplifier of claim 1, further comprising:
    an instrumentation amplifier having first and second inputs;
    a first transistor comprising a first input terminal, a first control terminal, and a first reference terminal, wherein the first transistor is coupled to a first sense electrode at the first input terminal and to the first input of the instrumentation amplifier at the first reference terminal through a first current path; and
    a second transistor having a second input terminal, a second control terminal, and a second reference terminal, wherein the second transistor is coupled to a second sense electrode at the second input terminal and to the second input of the instrumentation amplifier at the second reference terminal through a second current path,
wherein the first and second transistors are coupled to each other through a third current path between the first and second reference terminals,
wherein a voltage applied to the input terminal of the first transistor relative to the input terminal of the second transistor causes currents though the first, second and third current paths, and
wherein, when a current through the first or second current path causes a voltage of the first or second reference terminal to meet a control terminal to reference terminal threshold voltage for the first or second transistor, a remainder of the voltage applied to the input terminal of the first transistor relative to the input terminal of the second transistor that exceeds the control terminal to reference terminal threshold voltage will be between the first input and reference terminals or second reference and input terminals.

12. A medical device comprising:
    a sense amplifier that receives a differential voltage from first and second electrodes, outputs a voltage proportional to the differential voltage when the differential voltage is less than a predetermined threshold value, and outputs a substantially constant voltage when the differential voltage exceeds the predetermined threshold value; and
    a processor to process the output of the sense amplifier to sense a physiological signal of a patient,
wherein the sense amplifier comprises:
    a high pass filter comprising a capacitor and a resistor coupled in series, wherein a voltage applied across the resistor is proportional to the physiological electrical signal;
    an amplifier that amplifies an input voltage to generate an output voltage, wherein the input voltage is a function of the voltage applied to the resistor when the input voltage is less than a predetermined threshold value; and
    a feedback network comprising a transistor coupled in parallel with the resistor,
wherein the output voltage of the amplifier is coupled to a control terminal the transistor to activate the transistor when the input voltage exceeds the predetermined threshold value, and
wherein the transistor clamps the input voltage of the amplifier to a substantially constant value when the transistor is activated.

13. The medical device of claim 12,
wherein the input voltage exceeds the predetermined threshold value when therapeutic electrical stimulation is delivered to the body of the patient by the medical device or another medical device, and
wherein the sense amplifier has a recovery time of less than approximately one millisecond following delivery of the electrical stimulation.

14. The medical device of claim 12, wherein the predetermined threshold value is a function of a control terminal to reference terminal threshold value of the transistor.

15. The medical device of claim 12, wherein the clamped input voltage is approximately zero volts.

16. The medical device of claim 12, wherein, when the transistor is activated a pole of the high pass filter is shifted.

17. The medical device of claim 12, wherein, when the transistor provides a lower resistance current path for the capacitor to either discharge or charge when the transistor is activated to clamp the input voltage at the substantially constant value.

18. The medical device of claim 12,
wherein the feedback network comprise a time delay unit that applies a voltage to a control terminal of the transistor for a period of time after the transistor is activated, and wherein the voltage applied to the control terminal the transistor by the time delay unit biases the transistor to provide the lower resistance current path for the capacitor to either discharge or charge the capacitor for the period of time.

19. The medical device of claim 18, wherein the period of time ends at a time after the input voltage that exceeds the predetermined threshold value has ended.

20. The medical device of claim 12, wherein the medical device comprises at least one of a pacemaker, a cardioverter, a defibrillator, a cardiac monitor, or a neurostimulator.

21. The medical device of claim 20, wherein the medical device comprises an implantable medical device.

22. The medical device of claim 20, wherein the medical device comprises an external medical device.

23. A medical system comprising:
a first medical device configured to deliver an electrical stimulation signal to a patient;
a second medical device configured to sense a physiological electrical signal of the patient, the second medical device comprising:
a sense amplifier that receives a differential voltage from first and second electrodes, outputs a voltage proportional to the differential voltage when the differential voltage is less than a predetermined threshold value, and outputs a substantially constant voltage when the differential voltage exceeds the predetermined threshold value, wherein the electrical stimulation signal delivered by the first medical device causes the differential voltage to exceed the predetermined threshold value; and
a processor to process the output of the sense amplifier to sense a physiological signal of a patient,
wherein the sense amplifier comprises:
a high pass filter comprising a capacitor and a resistor coupled in series, wherein a voltage applied across the resistor is proportional to the physiological electrical signal;
an amplifier that amplifies an input voltage to generate an output voltage, wherein the input voltage is a function of the voltage applied to the resistor when the input voltage is less than a predetermined threshold value; and
a feedback network comprising a transistor coupled in parallel with the resistor,
wherein the output voltage of the amplifier is coupled to a control terminal of the transistor to activate the transistor when the input voltage exceeds the predetermined threshold value, and
wherein the transistor clamps the input voltage of the amplifier to a substantially constant value when the transistor is activated.

24. The medical system of claim 23, wherein the sense amplifier of the second medical device has a recovery time of less than approximately one millisecond following delivery of the electrical stimulation by the first medical device.

25. The medical system of claim 23, wherein the first and second medical devices comprise implantable medical devices.

26. The medical system of claim 23, wherein the first medical device comprises an implantable medical device and the second medical device comprises an external medical device.

27. The medical system of claim 23, wherein the first medical device comprises an external medical device and the second medical device comprises an implantable medical device.

* * * * *